(12) United States Patent
Hemphill et al.

(10) Patent No.: US 11,116,249 B2
(45) Date of Patent: Sep. 14, 2021

(54) SINGLE-SERVE SMOKING SYSTEM, DEVICES, KIT, AND METHODS

(71) Applicants: Mark Alan Hemphill, Baltimore, MD (US); Marcelo Torres, Samborondon (EC)

(72) Inventors: Mark Alan Hemphill, Baltimore, MD (US); Marcelo Torres, Samborondon (EC)

( * ) Notice: Subject to any disclaimer, the term of this patent is extended or adjusted under 35 U.S.C. 154(b) by 869 days.

(21) Appl. No.: 15/704,858

(22) Filed: Sep. 14, 2017

(65) Prior Publication Data

US 2018/0070629 A1    Mar. 15, 2018

Related U.S. Application Data

(60) Provisional application No. 62/558,108, filed on Sep. 13, 2017, provisional application No. 62/394,519, filed on Sep. 14, 2016.

(51) Int. Cl.
*A24F 1/00* (2006.01)
*A61M 16/12* (2006.01)
(Continued)

(52) U.S. Cl.
CPC .............. *A24F 1/00* (2013.01); *A24F 1/04* (2013.01); *A61K 36/185* (2013.01);
(Continued)

(58) Field of Classification Search
None
See application file for complete search history.

(56) References Cited

U.S. PATENT DOCUMENTS 1,908,878 A * 5/1933 Abrams .................... A24F 1/00
                                                        131/201
3,220,748 A * 11/1965 Moulton ................ B62K 15/00
                                                        280/287

(Continued)

OTHER PUBLICATIONS

Filing Receipt and Specification of U.S. Appl. No. 62/558,108, filed Sep. 13, 2017, 120 pages.
(Continued)

*Primary Examiner* — Michael J Felton
(74) *Attorney, Agent, or Firm* — Conley Rose, P.C.; Rodney B. Carroll

(57) ABSTRACT

A method of making a prepackaged, combustible unit of a plant based material for use in an inhalation system, metered dose inhaler, or dry powder inhaler. The method includes creating and shaping a combustible material packaging by processing leaves or plant fibers into a fibrous sheet, steaming the fibrous sheet, and using a female mold and a corresponding male mold to shape the combustible material packaging. The method further discloses filling pockets disposed within the combustible material packaging with the combustible material and sealing the combustible material packaging around the combustible material to create a prepackaged, combustible unit. Additional embodiments include various inhalation devices, inhalation systems, kits having instruction as to using the inhalation device, and methods of making the prepackaged combustible unit, and methods for using the inhalation devices.

23 Claims, 26 Drawing Sheets

(51) Int. Cl.
   *A61M 15/00* (2006.01)
   *A24F 1/04* (2006.01)
   *A61K 36/185* (2006.01)
   *A61M 16/14* (2006.01)
   *A61M 11/04* (2006.01)
   *A61M 16/00* (2006.01)

(52) U.S. Cl.
   CPC ........ *A61M 11/048* (2014.02); *A61M 15/002* (2014.02); *A61M 15/003* (2014.02); *A61M 15/0086* (2013.01); *A61M 16/127* (2014.02); *A61M 16/14* (2013.01); *A61M 16/0066* (2013.01); *A61M 2202/064* (2013.01)

(56) References Cited

U.S. PATENT DOCUMENTS

| | | | | |
|---|---|---|---|---|
| 3,863,648 | A | * | 2/1975 | Cathey ................ A24F 1/02 131/186 |
| 4,944,317 | A | * | 7/1990 | Thal .................... A24D 1/14 131/348 |
| 5,875,784 | A | * | 3/1999 | Allison ................ A24F 3/00 131/181 |

OTHER PUBLICATIONS

Filing Receipt and Specification of U.S. Appl. No. 62/394,519, filed Sep. 14, 2016, 45 pages.

\* cited by examiner

Fig. 1A(ii)
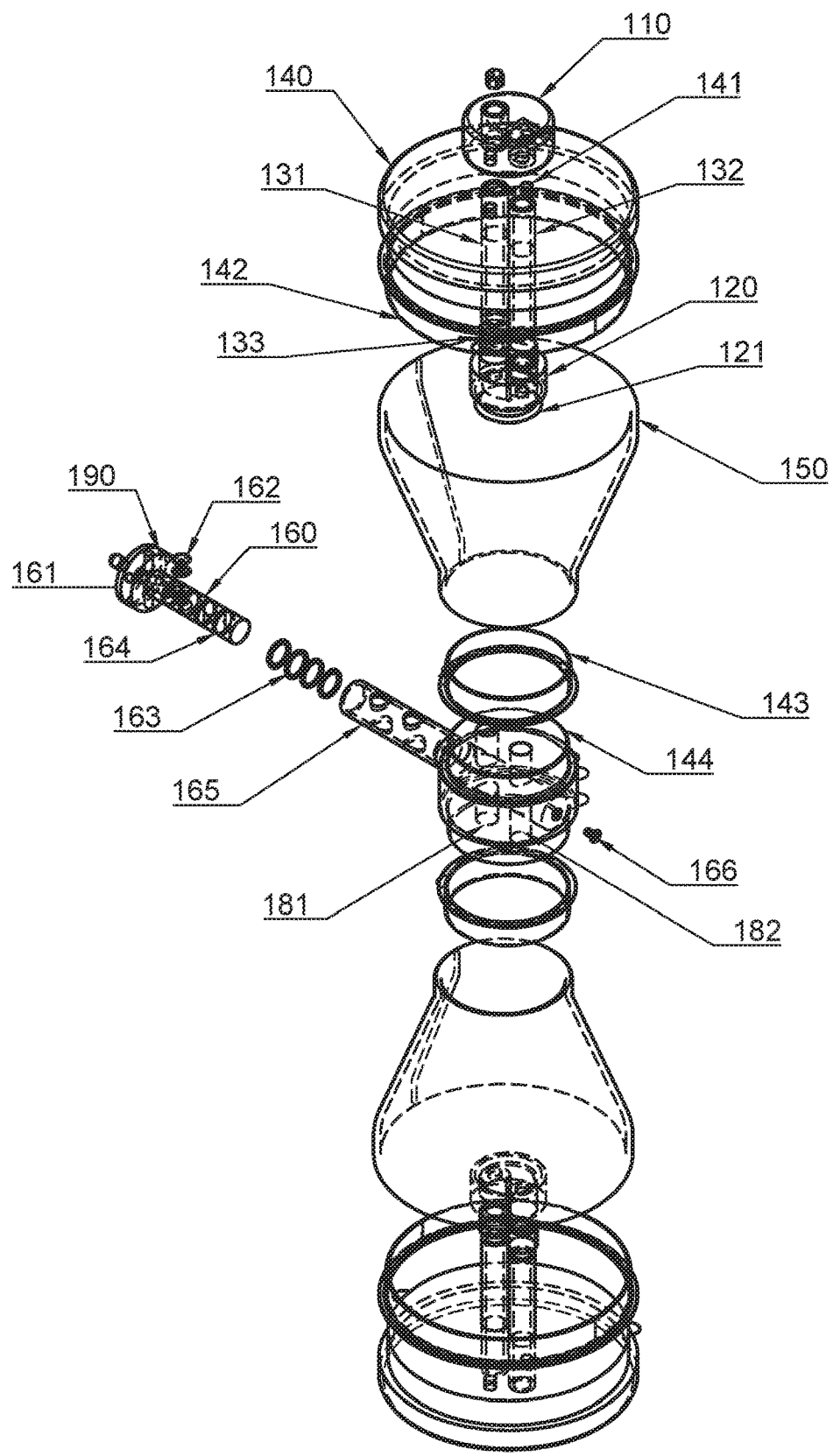

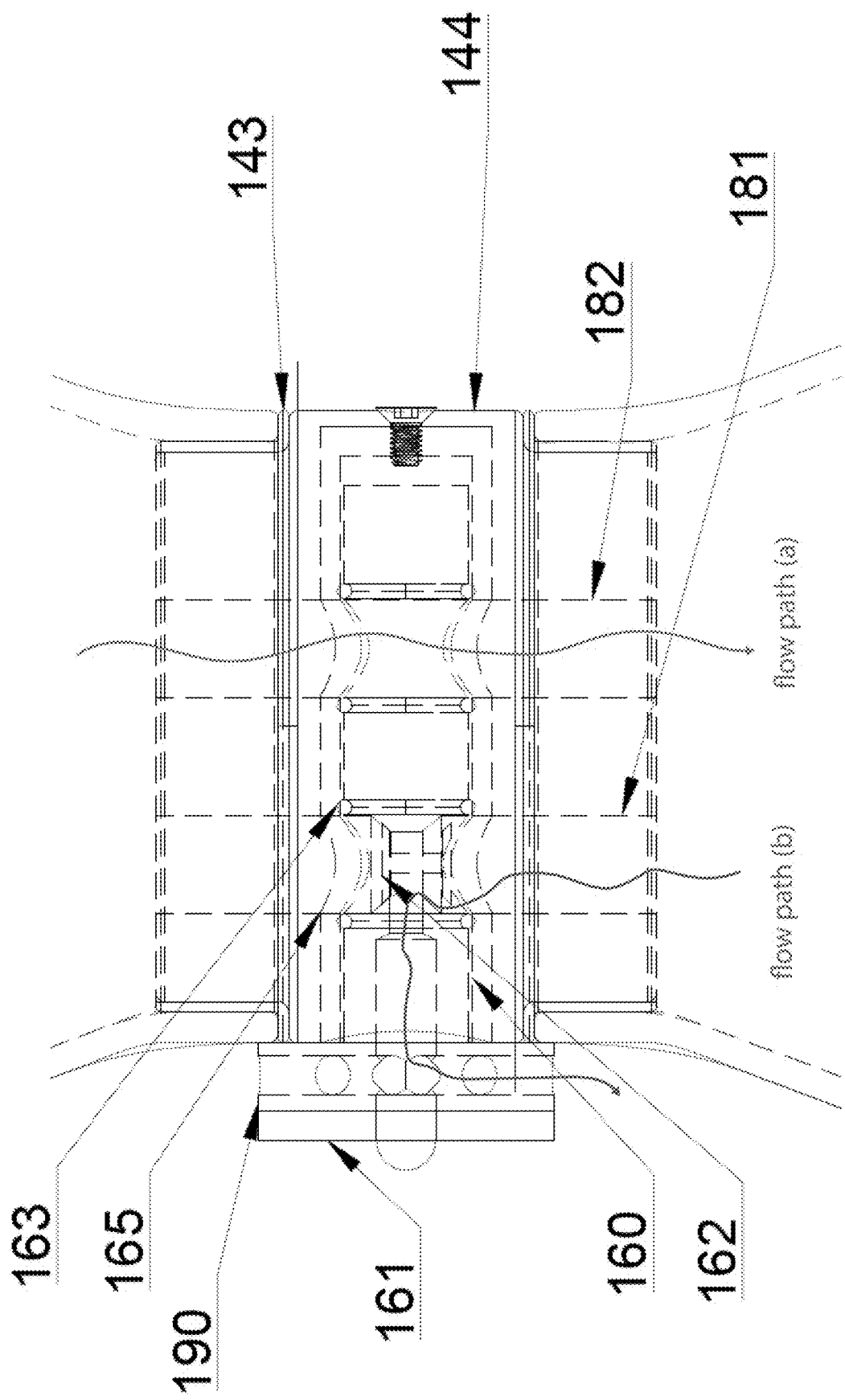

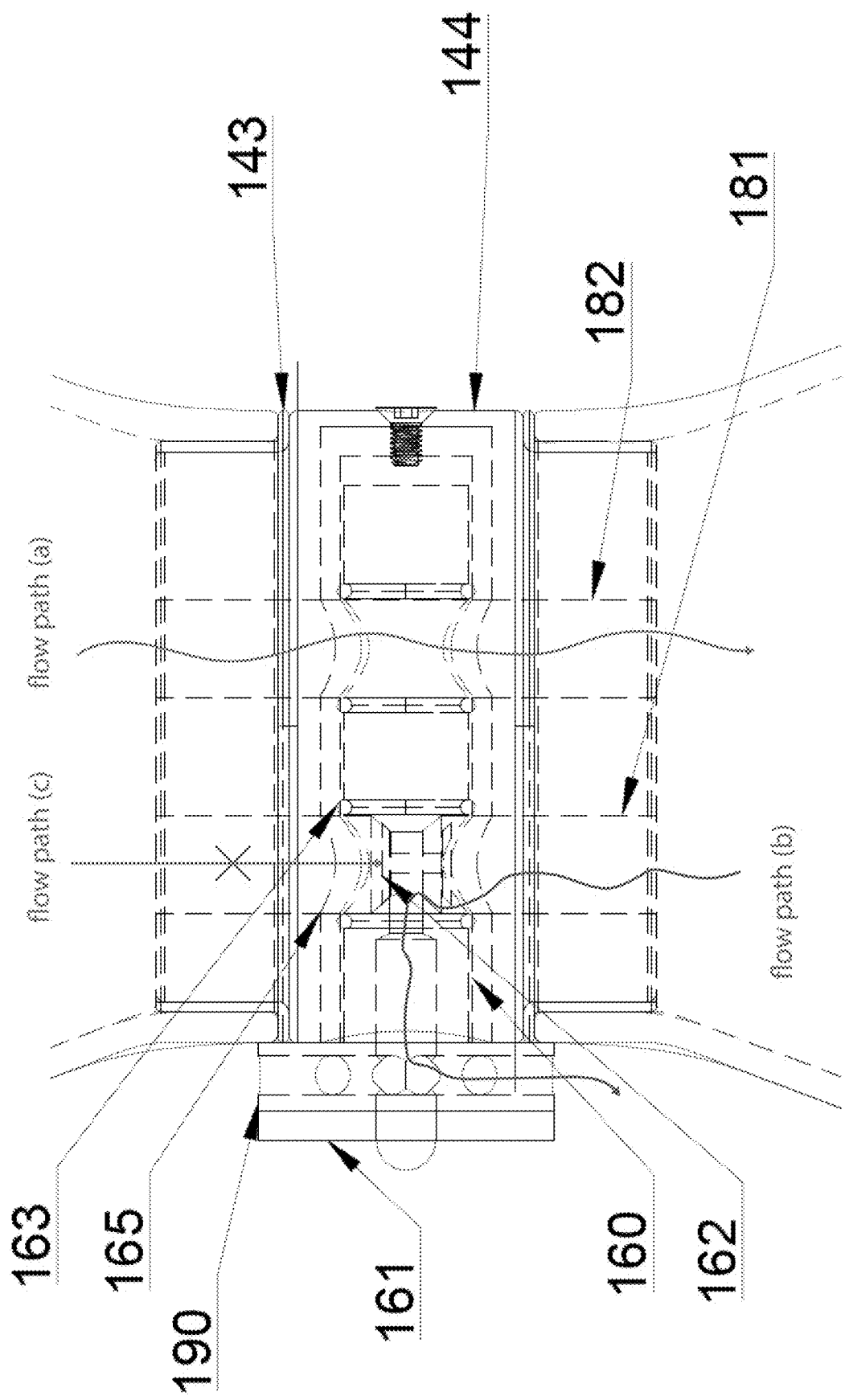

Fig. 3A(ii)
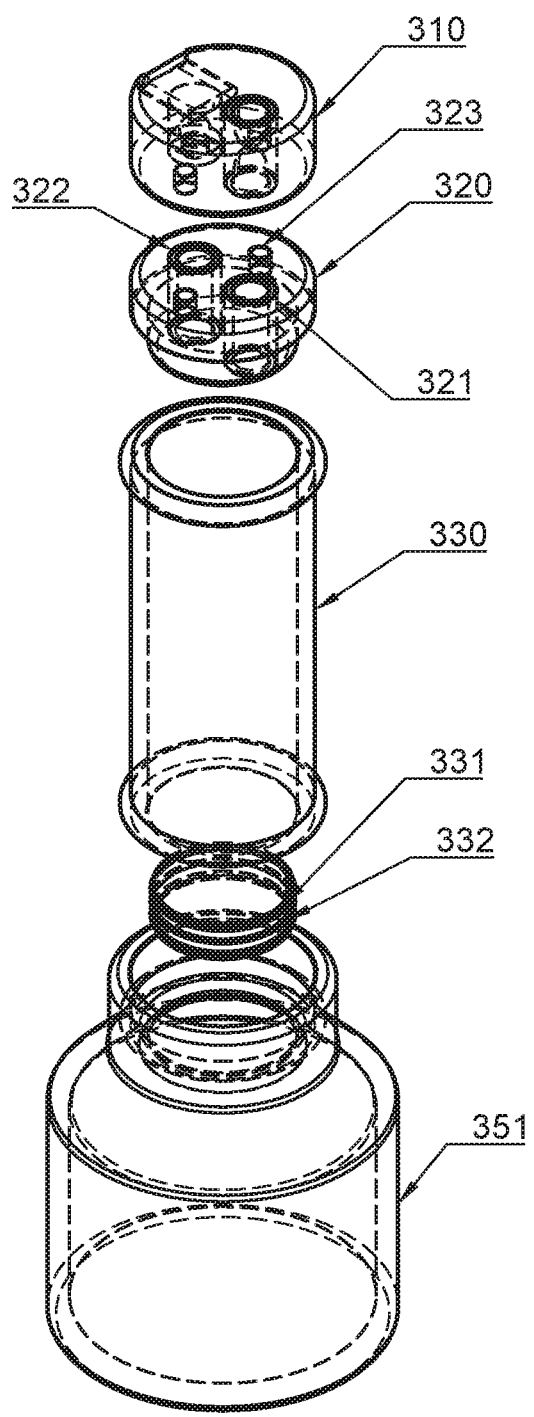

Fig. 4A
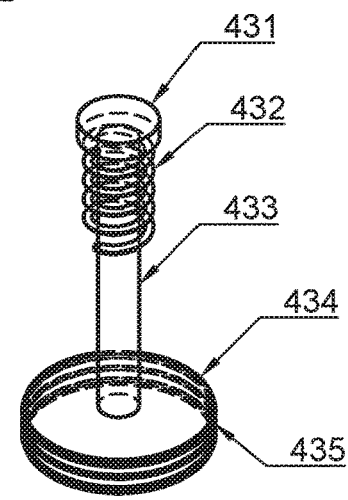
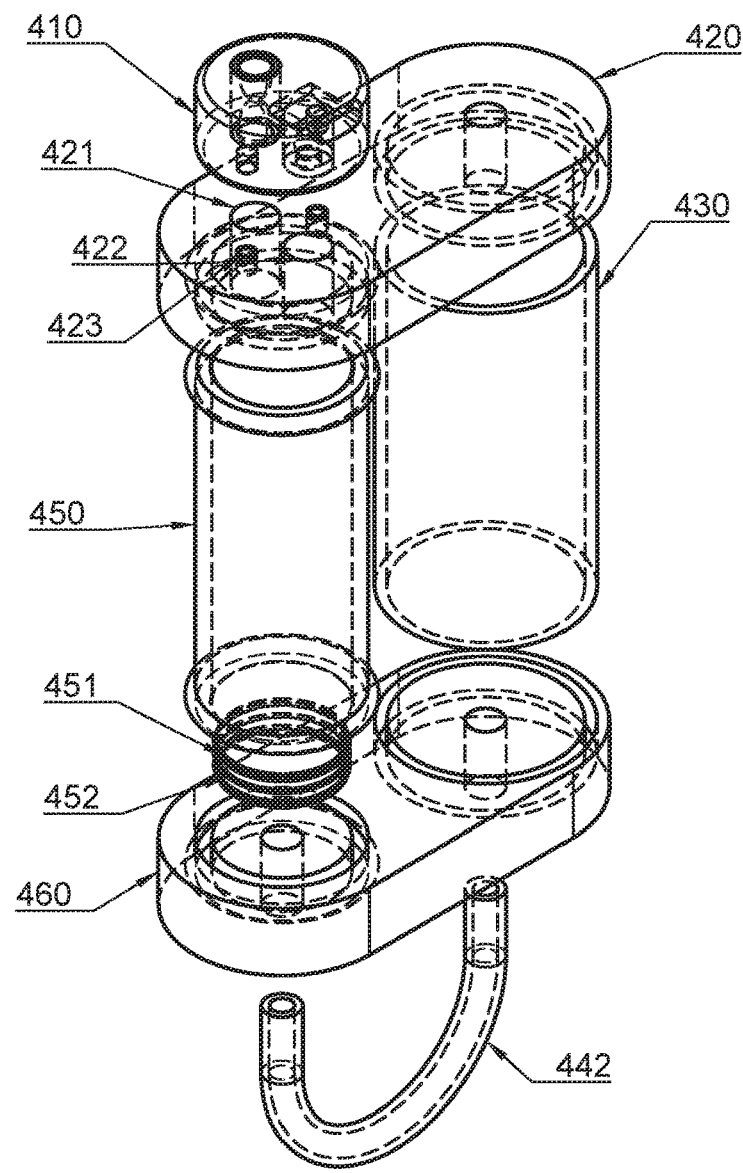

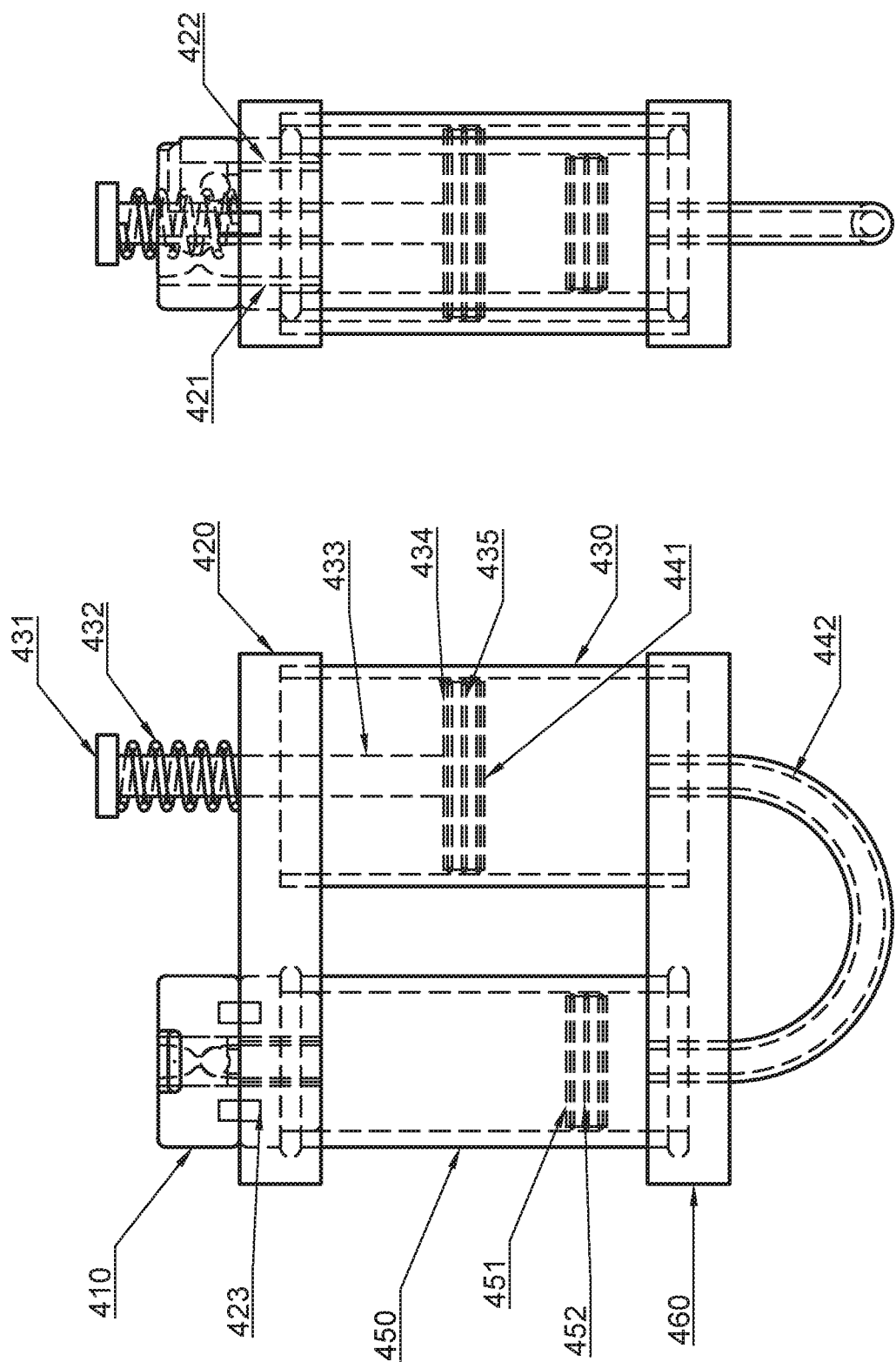

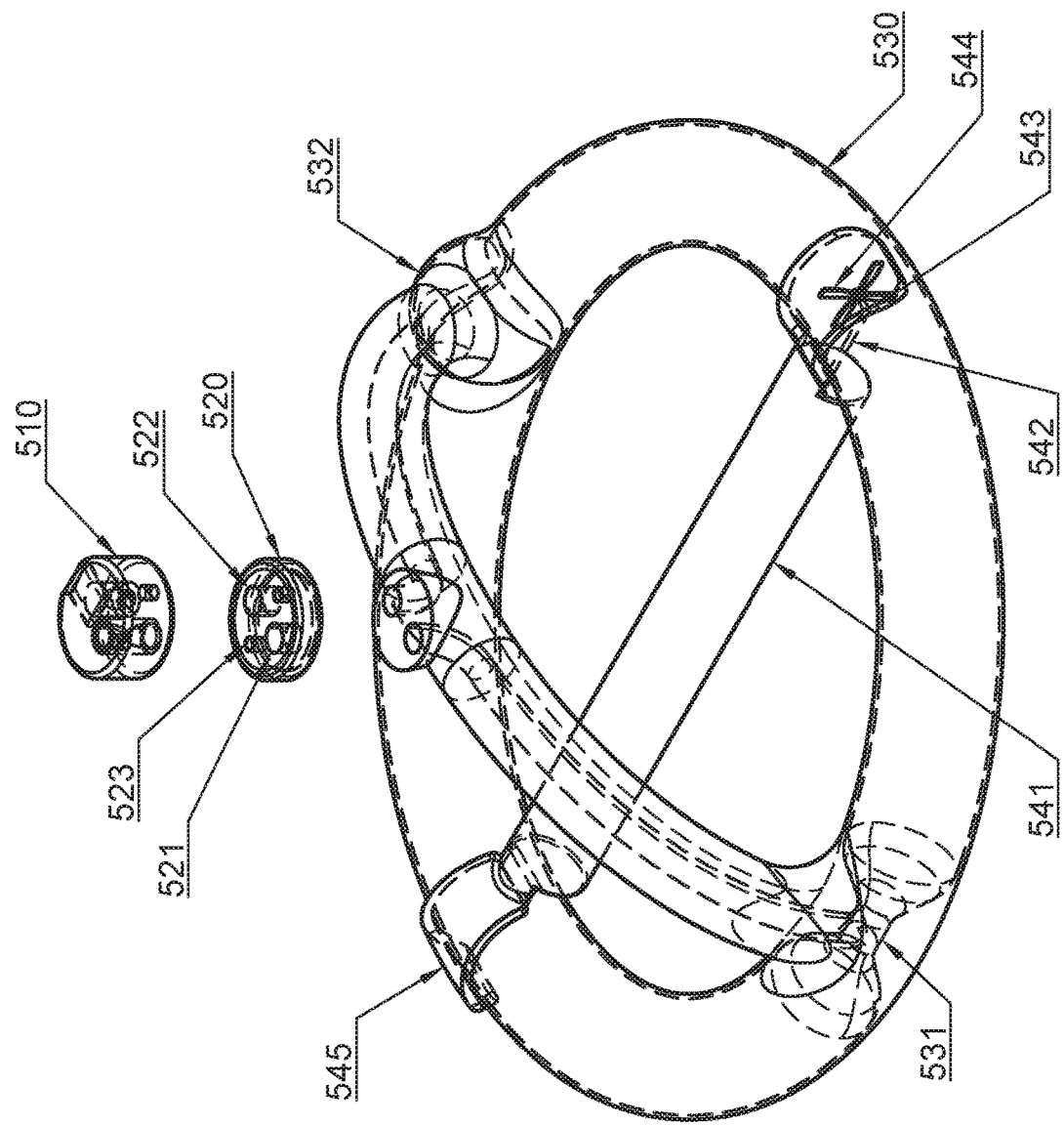

Fig. 6A(ii)
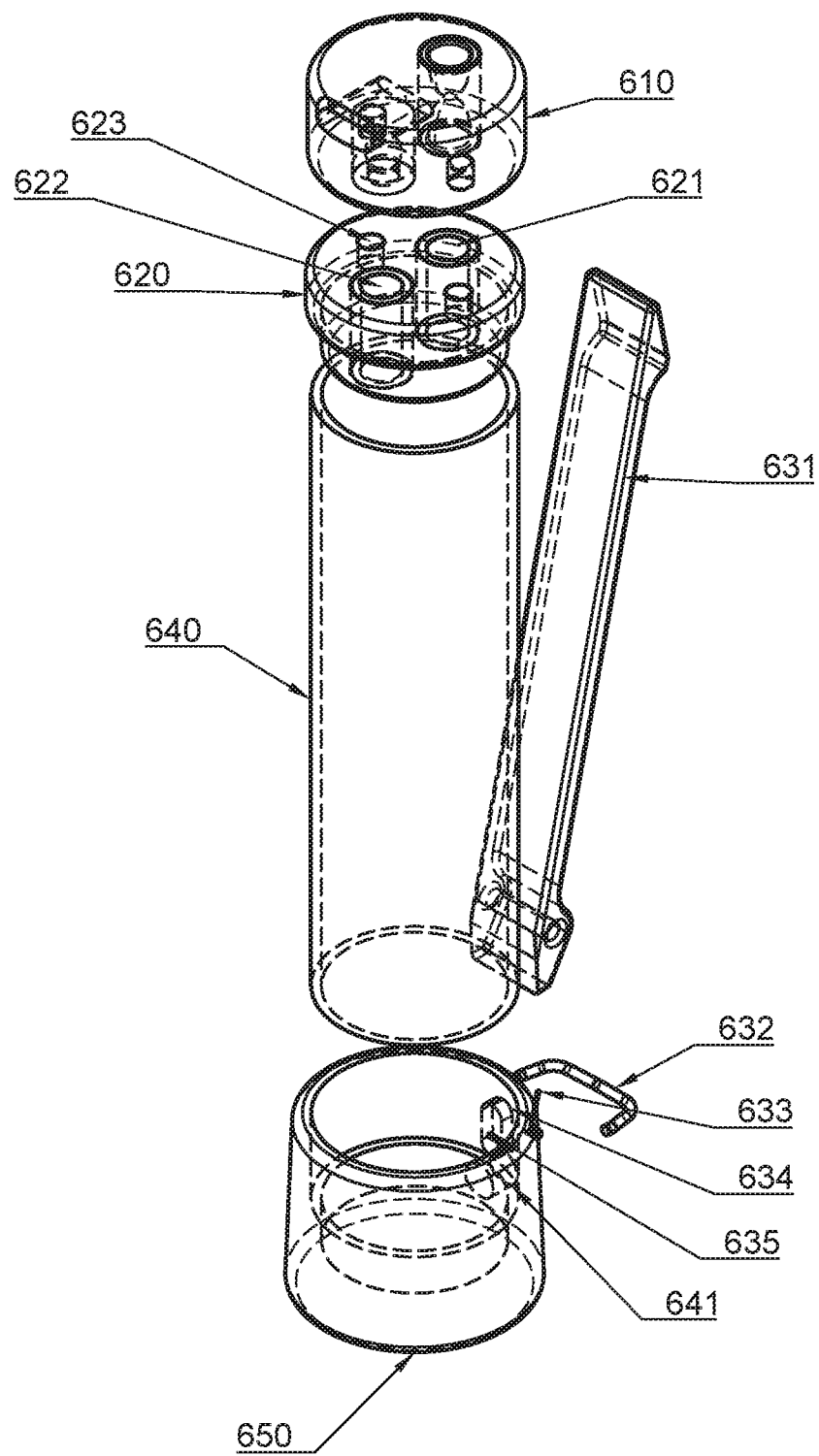

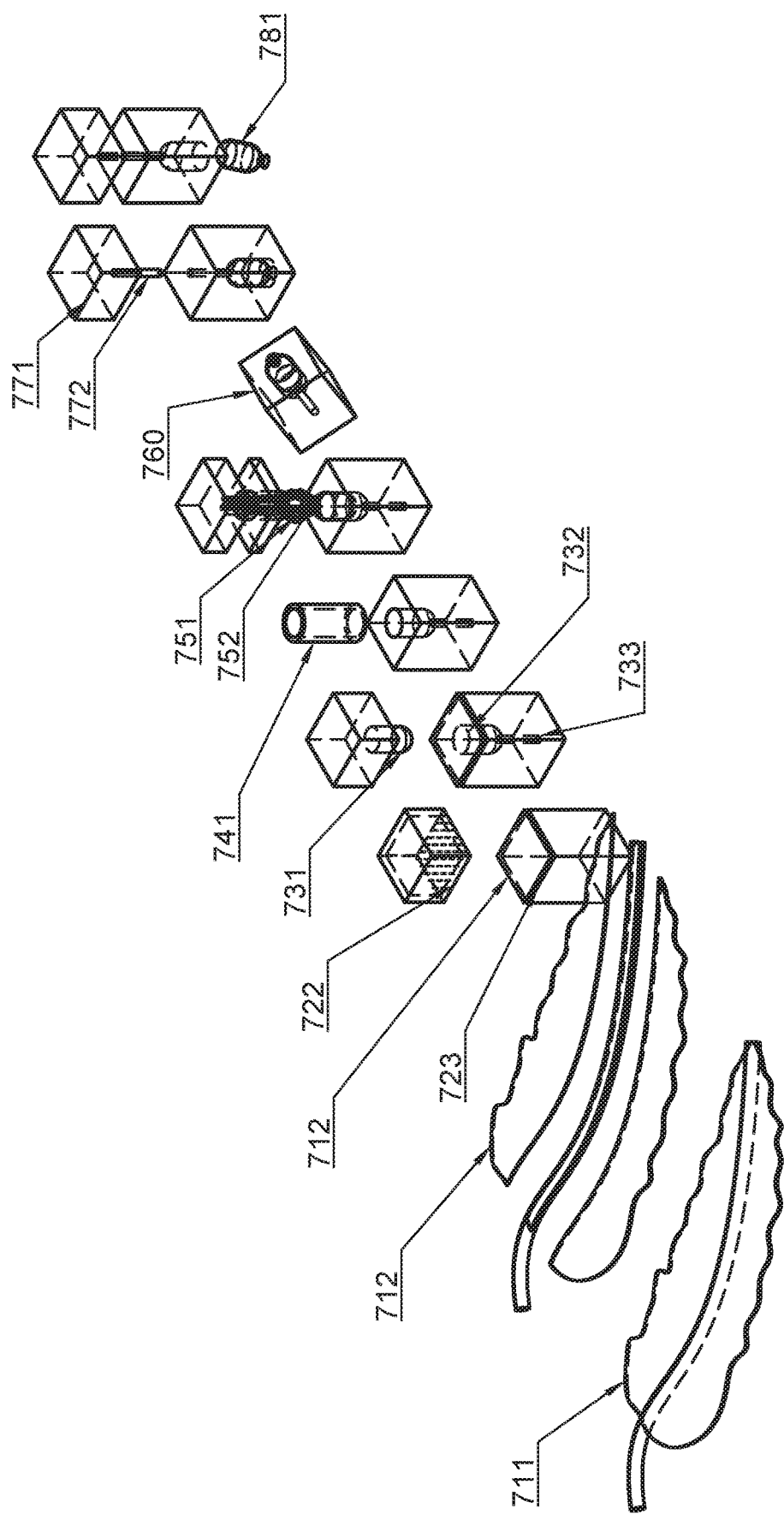

SINGLE-SERVE SMOKING SYSTEM, DEVICES, KIT, AND METHODS

CROSS-REFERENCE TO RELATED APPLICATIONS

The present application is a non-provisional of and claims priority to U.S. Provisional Patent Application Nos. 62/394,519 filed on Sep. 14, 2016, and 62/558,108 filed on Sep. 13, 2017, both entitled "Single-Serve Smoking System, Devices, Kit, and Methods" each of which is incorporated by reference herein in its entirety.

FIELD OF INVENTION

The subject matter disclosed herein relates to systems and methods for processing, combusting and inhaling materials, for either medical or recreational purposes.

BACKGROUND

Various active substances (e.g. alcohol, pharmaceuticals, etc.) are often consumed in particular serving sizes, for example, in single servings. However, no such system yet exists which delivers a particularized serving size, for example, a single serving, of a combusted and/or pyrolyzed combustible substances (e.g., smoke). As such, there is a need for systems of prepackaged material and inhalation devices disclosed herein addresses this need.

SUMMARY

According to an embodiment of this disclosure, a method of making a prepackaged, combustible unit of a plant based material for use in an inhalation system, metered dose inhaler, or dry powder inhaler is disclosed. The method includes processing leaves or plant fibers into a fibrous sheet, creating and shaping a combustible material packaging by processing leaves or plant fibers into a fibrous sheet, steaming the fibrous sheet, and using a female mold and a corresponding male mold to shape the combustible material packaging. The method further discloses filling pockets disposed within the combustible material packaging with the combustible material and sealing the combustible material packaging around the combustible material to create a prepackaged, combustible unit.

According to another embodiment of this disclosure, a modular metered dose inhaler comprising a top releasably connected to a base, the base having a variable internal volume; the top having a combustion bowl configured to receive and combust combustible material to produce smoke, the combustion bowl in fluid communication with the variable internal volume of the base such that the smoke travels from the combustion bowl to the internal volume of the base; and the top having an inhalation aperture. The metered dose inhaler wherein the inhalation aperture in one-way fluid communication with the variable internal volume of the base such that smoke travels from the internal volume of the base to a user via the inhalation aperture, wherein the variable internal volume is varied in response to (i) a mechanically induced input by a user and/or (ii) fluid flowing through the internal volume of the base, and wherein in response to varying the internal volume, a metered quantity of smoke is stored within the internal volume of the base.

According to another embodiment of the disclosure, a method of using a metered dose inhaler comprising a top releasably connected to a base, the base having a variable internal volume, the method comprising filling a chamber portion of the base with water; connecting the top to the base using releasable connectors to confirm orientation. The method of using the metered dose inhaler further comprising placing one unit of prepackaged combustible material into a combustion bowl disposed in the top, the combustion bowl configured to receive and combust the combustible material to produce smoke, and the combustion bowl in fluid communication with the variable internal volume of the base such that the smoke travels from the combustion bowl to the internal volume of the base. The method of using further comprising activating the device to enable fluid to flow from the combustion bowl and into the variable internal volume of the base; holding a flame to the prepackaged combustible material, causing combustion thereof; and after observing the prepackaged material combust fully, inhaling the smoke through an inhalation aperture disposed in the top, the inhalation aperture in one-way fluid communication with the variable internal volume of the base such that smoke travels from the internal volume of the base to a user via the inhalation. The method of using the metered dose inhaler further comprising equalizing pressure in the chamber portion from which smoke is being inhaled by a continued activation of the device.

Additional embodiments include various inhalation devices, inhalation systems, kits having instruction as to using the inhalation device, and methods of making the prepackaged combustible unit, and methods for using the inhalation devices as discussed further below.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

FIG. 1A(ii) illustrates an exploded three dimensional view of the parts of an "hourglass" style inhalation device, according to an embodiment of this disclosure.

FIG. 1D illustrates a view of an inhalation device having a button positioned in an activated flow position, according to an embodiment of this disclosure.

FIG. 1E illustrates a view of an inhalation device having a double anti-gravity valve, according to an embodiment of this disclosure.

FIG. 3A(ii) illustrates an exploded three dimensional view of the parts of a "squeeze" style inhalation device, according to an embodiment of this disclosure.

FIG. 4A illustrates an exploded three dimensional view of the parts of a "pipette" style inhalation device, according to an embodiment of the disclosure.

FIG. 4B(i) illustrates a side view of a "pipette" style inhalation device in an assembled position, according to an embodiment of this disclosure.

FIG. 4B(ii) illustrates an end view of a "pipette" style inhalation device in an assembled position, according to an embodiment of this disclosure.

FIG. 5 illustrates an exploded three dimensional view of the parts of a "venturi" style inhalation device, according to an embodiment of this disclosure.

FIG. 6A(ii) illustrates an exploded three dimensional view of the parts of a "lever" style inhalation device, according to an embodiment of this disclosure.

FIG. 7 illustrates a system for making a single prepackaged combustible, single-serving material unit, according to an embodiment of this disclosure.

DETAILED DESCRIPTION

Disclosed herein are one or more embodiments of a system for a delivery of a single serving or dosage (e.g., a predetermined, particularized, and/or prescribed amount; a metered dose) of a combusted and/or pyrolyzed combustible substances (e.g., smoke), referred to herein as a "single-serving system." In various embodiments of this disclosure, smoke is defined as a product of burning materials; for example, one or more airborne products (solids, liquids, gases) emitted and/or produced upon combustion of a material. In one or more of the embodiments disclosed herein, the disclosed single-serving system generally includes an inhalation device and a unit of a prepackaged combustible material (also referred to herein as, for example, a nano-joint).

The inhalation device generally comprises of two modules (each of which may be comprised of several submodules), particularly, a base module and a cap module. The cap module and base module, as will each be disclosed herein, may be configured such that a given cap module is usable with multiple base modules of various configurations (e.g., any inhalation device base module disclosed herein). In an embodiment, the cap module is generally configured to regulate air flow into or out of the base module and to retain the prepackaged material such that, when combusted, smoke from the prepackaged material is drawn into an internal volume of the base module. The base module is generally configured to supply, at the demand of the user, a constant pressure gradient, for example, so as to draw air into an internal space thereof via the cap module, for example, for a consistent and/or predetermined period of time.

The cap module generally comprises two apertures or tubes which permit air flow. The first aperture in the cap receives the prepackaged combustible material (or loose combustible material, per the user's discretion) and permits air flow from the ambient environment into the base module's internal volume. More particularly, and as will be disclosed herein, the cap module generally comprises a recess within the first aperture. The recess in the first aperture is generally configured to retain a unit and/or quantity of prepackaged combustible material that is sized and shaped such that it fits therein. The second aperture serves as the access point from which the user may inhale; it does not, however, permit flow into the base module's internal volume.

Figure 2:
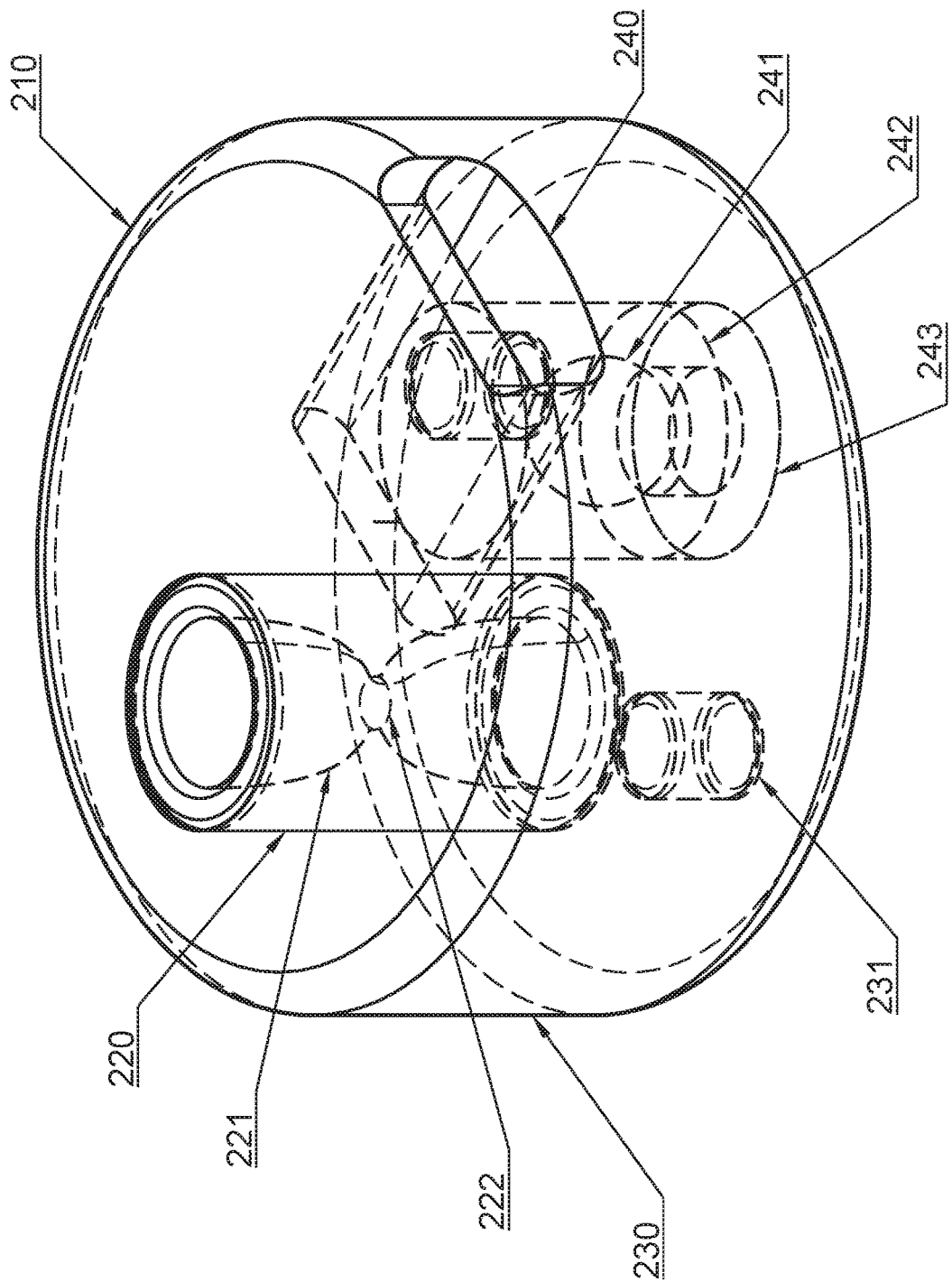
FIG. 2 illustrates a standard cap module for use in an inhalation device, according to an embodiment of the disclosure.

Referring to FIG. 2, an embodiment of the cap module is illustrated. In the embodiment of FIG. 2, the cap module 210 generally comprises a cap module body 230, an ingress tube 220, and an inhalation aperture 240 (also referred to herein as, for example, an egress slot).

The ingress tube 220 includes a constriction 222 in the interior diameter of the ingress tube 220, for example, so as to at least partially define a bowl 221. The bowl 221 (also referred to herein as, for example, a combustion bowl) is configured to receive and retain a prepackaged combustible material while air is drawn through the ingress tube 220 and into the base module, as will be disclosed herein. In another embodiment, the bowl 221 is configured to receive and retain loose material, for example, material that is ground, chopped, shredded, powdered, foamed, crystalline, whole, or a combination of these.

The inhalation aperture 240 of the cap module 210 is generally configured to permit air-flow exclusively in one direction, particularly, from an internal volume of a base module to which the cap module is connected, outward (e.g., to a user, for example, into a user's respiratory system). For example, in various embodiments, the inhalation aperture 240 includes a suitably configured directional valve (e.g. a one way valve or a check valve). In the embodiment of FIG. 2, for instance, the inhalation aperture 240 includes a spherical ball bearing 241 (e.g., a glass or metal ball bearing) and a ball seat 242 (e.g., a washer or recess sized to receive the spherical ball bearing 241, or a washer or recess having an inner diameter slightly smaller than the outer diameter of spherical ball bearing 241). In an alternative embodiment, other suitable directional valve configurations may be similarly employed (e.g., a flapper valve or the like). In another embodiment of the disclosure, the cap module 210 further comprises an aperture 243 having a diameter approximately equal to the exterior diameter of the ball seat 242.

Also illustrated in FIG. 2, an embodiment of the cap module includes one or more quick release connectors 231 to provide for releasable connection between the base module and the cap module, for example, a pair of magnets, a ¼ turn lug, a spring lug with a recess, a j-slot release, or the like. The pair of magnets 231 is configured so as to join (e.g., connect) the cap module 210 to a base module, for example, an inhalation device in a particular orientation and according to various embodiments of the disclosure. For example, the poles of the pair of magnets 231 may be oriented such that the cap module 210 may only be attached to the base module or inhalation device in a particular, preconfigured alignment.

The cap module 210 is configured to be used with any of a number of various inhalation devices, as discussed further below. For example, the cap module 210 may be used with an inhalation device having an "hourglass" style, a "squeeze" style, a "pipette" style, a "venturi" style, or a "lever" style.

In use, the base module is configured such that, when the prepackaged combustible material retained in the cap module is ignited (e.g. via a standard lighter), this constant pressure gradient applied over a consistent time period results in an even and complete combustion of the prepackaged combustible material retained within the cap module. The resulting quantity of smoke (e.g., resulting from combustion of the prepackaged combustible material), is thereby mechanically prepared for the user, and is contained within the internal volume of the base module until such time the user decides to receive the smoke via the inhalation aperture.

Upon activation by the user, the base module of the inhalation system replicably supplies a constant pressure gradient for a consistent period of time, drawing into its internal volume a given amount of smoke originating from the material (prepackaged or loose) combusting within the recess aperture of the cap module. Various mechanical means may be employed to supply this constant pressure gradient for a consistent period of time, several of which are described in the embodiment configurations below.

As noted above, the disclosed inhalation devices are suitable for the delivery of a single-serve quantity of smoke, also referred to herein as a measured dose, a metered dose, or a nano-joint. As will be apparent to the person of ordinary skill in the art upon viewing this disclosure, the delivery of such a single-serve quantity of smoke is made possible, firstly, by limiting the volume of combustible material which can fit in the device, whether prepackaged or loose (e.g., by the cap module). Secondly, the delivery of such a single-serve quantity of smoke is made possible via a constant pressure gradient that is generated by the device (e.g., by the base module) such that, when activated, the pressure gradient is approximately equal to the difference between the atmospheric pressure and the internal pressure (e.g., generated by the base module): $\Delta P = P_{external} - P_{internal} \approx k_1$, where $P_{external}$ is the atmospheric pressure, $P_{internal}$ is the pressure within the chamber abutting the ingress aperture, and $k_1$ is some constant. For example, under most circumstances, this pressure gradient ($\Delta P$) is approximately a constant ($\approx k_1$). This substantially constant pressure gradient is achieved by ensuring that $$\frac{dV_{internal}}{dt} \approx k_2,$$

where $V_{internal}$ is the internal volume of the chamber into which the smoke from combusting material is pulled, and $k_2$ is some constant. In other embodiments, this constant pressure gradient ($k_1$) may also be achieved by other mechanical means (e.g. the venturi effect). Whether supplied by gravitational, hydraulic, some other force, this constant pressure gradient applied to the combustion of a small, fixed volume of material (for a duration of time sufficient to combust said material entirely) replicably generates a single-serve volume or packet of smoke (e.g., a measured or metered dose). This class of devices is thus of value for both recreational and medicinal preparation of a combustible material for inhalation.

Figure 1A:
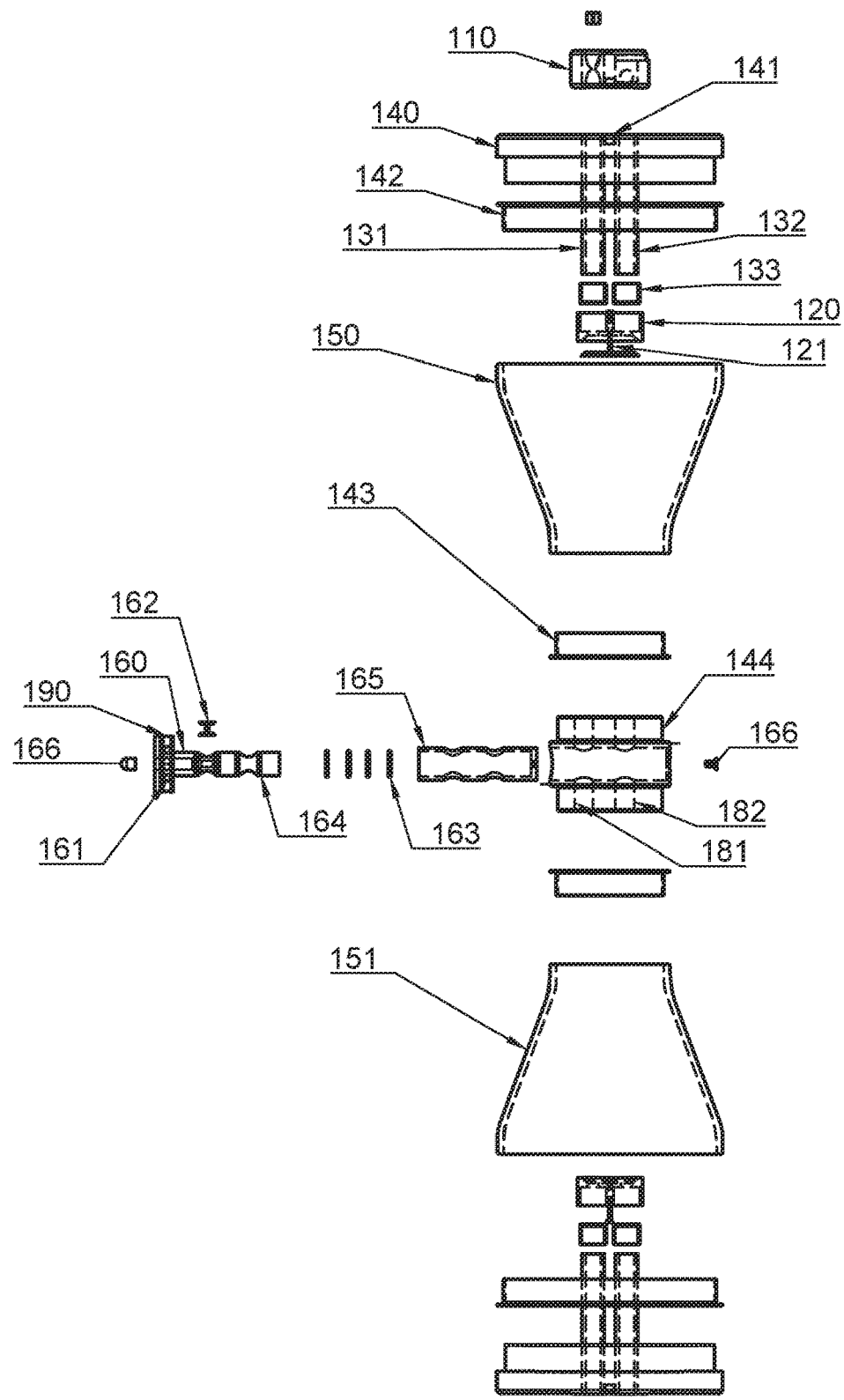
FIG. 1A(i) illustrates an exploded side view of the parts of an "hourglass" style inhalation device, according to an embodiment of this disclosure.

Referring to FIGS. 1A(i)-1D, a first embodiment of inhalation device is illustrated. In the embodiment of FIGS. 1A(i)-1D, the inhalation device base module comprises an "hourglass" configuration. FIG. 1A(i) depicts an exploded side view of the parts of an "hourglass" style inhalation device and FIG. 1A(ii) depicts an exploded three dimensional view of the same. The base module generally includes a body having two generally symmetrical halves and thereby defining two chambers: a top chamber 150 and a bottom chamber 151. Each of the two chambers (e.g., the top chamber 150 and the bottom chamber 151) substantially defines an internal volume, and are in fluid communication with various apertures. Hereinafter, these aperture pairs will be referred to as "cap apertures" and "button apertures," reflecting the modules to which the apertures lead, respectively. The apertures leading to the cap include one-way valves which preferentially permit air inflow into the chamber, and always prevent liquid outflow. Regarding the "button apertures," they are valveless, leading directly into the horizontal aperture in which the button resides.

In the embodiment of FIGS. 1A(i) and 1A(ii), the base module is configured such that water falls from a top chamber 150 to a bottom chamber 151 and, thereby, creates a constant pressure gradient within the top chamber 150. This pressure gradient pulls smoke from the combusting prepackaged (alternatively, loose) material residing in the recess (e.g., bowl 221) of the ingress tube (e.g., ingress tube 220) of the cap module 110. FIG. 1D illustrates a view of the inhalation device of FIGS. 1A(i) and 1A(ii) showing the flow paths when a button 190 is depressed by a user and fluid communication is enabled between the top chamber 150 and the bottom chamber 151. When fluid flow between the top chamber 150 and bottom chamber 151 is activated, fluid communication is also opened or permitted between the bottom chamber 151 and an ambient atmosphere outside of the hourglass inhalation device.

As shown in FIG. 1D, flow path (a) illustrates the flow of water that falls from the top chamber 150 to the bottom chamber 151 when the device is in the activated position. Flow path (b) illustrates a flow path of air which escapes from the bottom chamber 151 to the atmosphere outside the inhalation device when the device is in the activated position, making room for the incoming water flowing from the top chamber 150 to the bottom chamber 151.

As shown in FIGS. 1A(ii)-1B, the cap module 110 is releasably connected to the base module, for example, via a suitable docking submodule 140 comprising a pair of magnets 141 configured to be joined to the corresponding magnets (e.g., magnets 231) of the cap module 110. The cap module and the base module comprise complementary engagement features to provide a quick release attachment of the standard cap module and base module. Less than 180, 160, 140, 120, 100, 90, 80, 70, 60, 50, 40, 30, 25, 20, 15, 10, 5, 3, 1 degrees of rotation of the standard cap module relative to the base module to engage the complementary engagement features. Complementary engagement features comprise magnets, spring loaded/biased lug and j-slot, and "coarse" threads. When joined together, the ingress tube (e.g., ingress tube 220) of the cap module 110 provides a route of fluid communication with an ingress tube 131 and, also, the inhalation aperture (e.g., inhalation aperture 240) of the cap module is in fluid communication with an egress tube 132 of the base module. The ingress tube 131 is generally configured to allow directional (e.g., one-way) fluid movement into the top chamber 150 of the base module. For example, in the embodiment of FIG. 1, a valve body 120 and valve plunger 121 permit fluid communication into and out of the top chamber 150, while preventing fluid communication into and out of the bottom chamber 151. The valve plunger 121 is translationally moveable within, but also bounded by, the valve body 120, with their relative position (and thus sealing characteristics) determined by gravity. Alternatively, other suitable directional valves may be similarly employed. The ingress and egress tubes fit within a sleeve 133, which themselves fit within the valve body 120. Similarly, an interface between the docking submodule 140 and the chambers 150 and 151 is comprised of a flanged sleeve 142. The ingress tube 131 also comprises a plurality of diffuser holes or orifices (not shown), for example, to disperse smoke into the internal volume (e.g., top chamber 150) of the base module.

A valve, for example, a translationally movable valve as will be disclosed herein, regulates flow between chambers. When the valve or button 190 is activated (i.e. moved horizontally, in the embodiment of FIG. 1A(i)), the "button shaft" 160 permits water to flow from the top chamber 150 to the bottom chamber 151 and, also, allows for air contained in the bottom chamber 151 to escape the device entirely. Once the water has fallen from the top chamber 150 to the bottom chamber 151, the user may inhale the smoke contained therein. During inhalation, the button 190 should remain activated, this time permitting external air to enter the uppermost section of the lower chamber on its way to the upper chamber (thereby refilling the space formerly occupied by the smoke inhaled by the user).

FIGS. 1A(i), 1A(ii), 1D, and 1E illustrate the button 190 in an activated state when fluid flow is allowed between the top chamber 150 and bottom chamber 150. The default position of button 190 is a "no flow" state such that neither water in the flow path (a) nor air in flow path (b) moved from its respective chambers. A spring mechanism or biasing force (e.g. the air trapped between the button shaft 160 and the button sheath 165) provides the force which ensures the button returns to the default (i.e. "no flow") position.

As shown in FIG. 1E, in order to accommodate the user turning the hourglass over without the contents of the device spilling (and without the user having to adjust the valve), the button 190 may feature a double anti-gravity valve 162. This double anti-gravity valve 162 is configured such that a series of apertures 161 connects the bottom chamber 151 with the device's immediate exterior or atmosphere. This arrangement of apertures and valves serves the purpose of allowing air in the bottom chamber to exit the device. The feature which permits water to flow from the top chamber 150 to the bottom chamber 151 is a simple vertical aperture extending through the button 190. When activated, these two apertures align with a pair of corresponding apertures 181 and 182 in both chambers of inhalation device or "the body". The interface between the button shaft 160 and the button sheath 165 may be sealed by o-rings 163, which nest within grooves 164 which are sized to securely, yet releasably hold the o-rings 163. The other end of the button shaft 160 is sealed by screw 166 (which may be removed in case the user wishes to remove the button shaft 160 from button sheath 165 for maintenance, etc.).

Referring to FIG. 1E, flow path (a) illustrates the flow of water that falls from the top chamber 150 to the bottom chamber 151 when the device is in the activated position (for example, when a user is depressing the button 190 and tilts or flips the device over) and water flows through aperture 182. Flow path (b) illustrates a flow path of air which escapes from the bottom chamber 151 to the atmosphere outside the inhalation device via aperture 181 when the device is in the activated position, making room for the incoming water flowing from the top chamber 150 to the bottom chamber 151. Flow path (c) with the "X" therein illustrates how water may try to go down aperture 181, but gets stopped or prevented from flowing by an upper plunger part of the double anti-gravity valve 162.

Figure 1B:
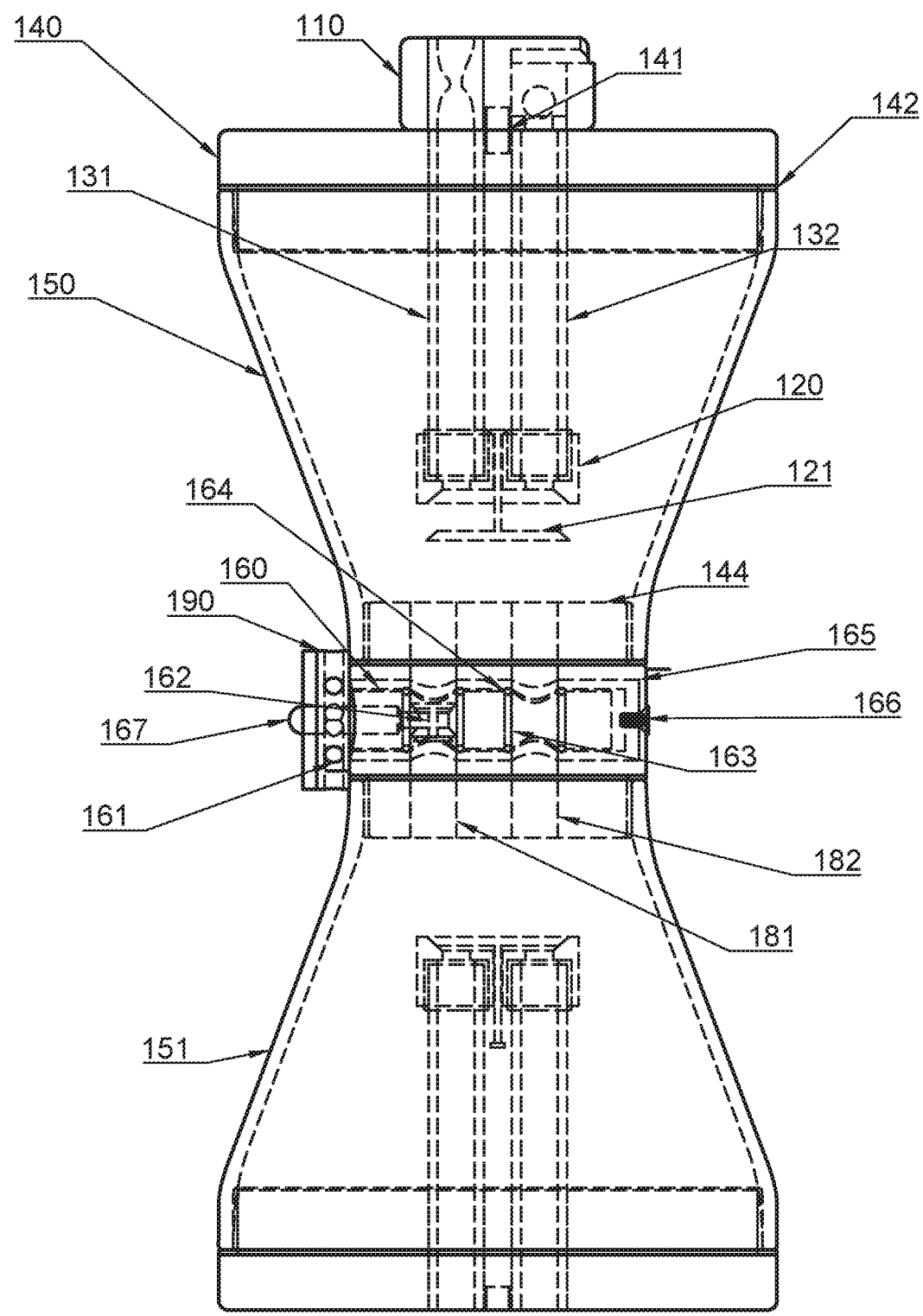
FIG. 1B illustrates a side view of an "hourglass" style inhalation device in an assembled position, according to an embodiment of this disclosure.

Further features related to FIGS. 1A(i)-1E include the button sheath 165 which fits within an appropriately sized aperture in a center block 144. A nub 167 (for example, an end of screw 166) is depicted in FIG. 1B and provides a tactile indication of the location of the button's center (and therefore the ideal position for the application of force to activate the device). As shown in FIG. 1A(i), second flanged sleeve 143 provides an interface between the top chamber 150 and the center block 144.

Figure 1C:
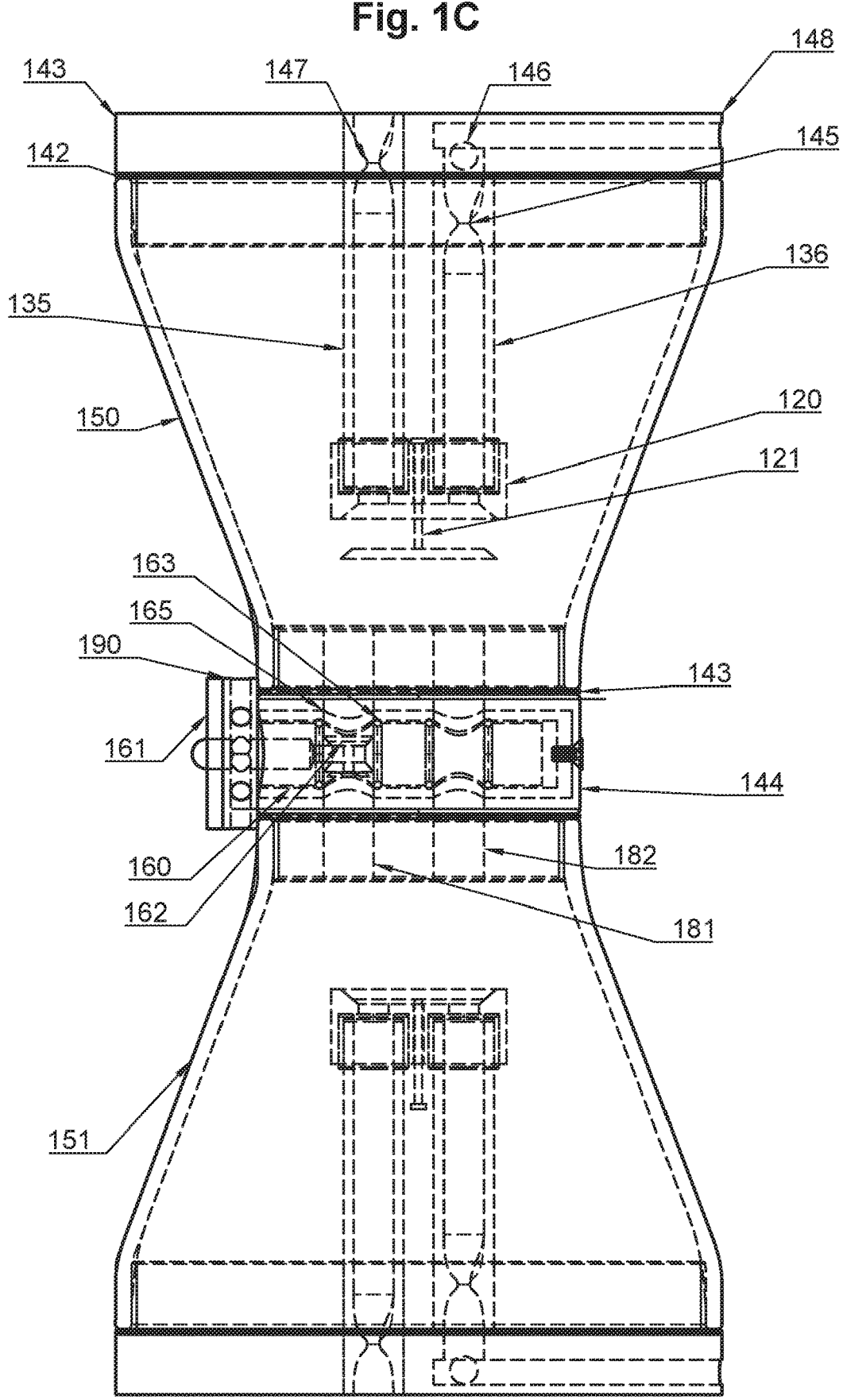
FIG. 1C illustrates a side view of an "hourglass" style inhalation device, according to another embodiment of this disclosure.

An alternate embodiment disclosed herein is illustrated in FIG. 1C. As shown in FIG. 1C, the hourglass configuration may utilize a structural submodule with integrated ingress and egress apertures 148. This structural submodule contains a bowl 147, a ball bearing 146, and an egress tube with a constriction with approximately circular cross section 145, all of which serve to replicate the functionality of the cap module 110 without requiring it.

In the "Squeeze" configuration, an elastically compressible bulb 351 hydraulically modulates the position of a plug 331 residing within a tube 330. At the other end of this tube is a top 320 designed to magnetically receive the standard cap module 310. When the bulb is squeezed, an incompressible fluid 341 (preferably water) presses the plug towards the top 320. Releasing (i.e. "unsqueezing") the bulb, then, draws the plug back towards the bulb, creating low pressure in the top portion of the tube (thereby drawing in combusting material from the cap module's bowl 221). Squeezing the bulb again causes the plug to move towards the tube's top again, this time assisting the user's inhalation by pressing smoke through the cap module's inhalation aperture 240.

The "Squeeze" configuration is comprised of four submodules (in addition to the standard cap module): a tube 330, a bulb 351 (for example, an elastically compressible bulb), a plug 331, and a top 320. The plug resides within the tube, which itself is releasably affixed to the bulb, with fluid 341 (e.g. water or another incompressible fluid) occupying the volume within the bulb and in the portion of the tube leading to the plug. O-rings 332 seal the interface between the plug 331 and the tube 330. The top 320 seals the end of the tube 330, containing an ingress tube 321 and an egress tube 322 disposed through the docking submodule 310, and a pair of magnets 323. The ingress tube 321 corresponds with ingress tube 220 of the standard cap module. The egress tube 322 corresponds with egress tube 240 of the standard cap module. The pair of magnets 323 corresponds with pair of magnets 231 of the standard cap module.

The "Pipette" configuration consists primarily of two tubes configured to be a first driving submodule 430 and a second driving submodule 450 (of different diameters and approximately equivalent lengths), connected by a smaller, flexible tube 442. This smaller, flexible tube 442 permits fluid flow between the first driving submodule and the second driving submodule which may be two larger tubes. The first driving submodule 430 may have a larger diameter than the second driving submodule 250 and may contain a plunger 434 with o-rings 435 which may be depressed (by the thumb of the user pressing button 431, connected to this plunger by plunger shaft 433) in order to cause a corresponding movement of a plunger 451 (e.g. a plunger sans shaft or a plug) with o-rings 452 residing within a second driving submodule 450, for example a tube having a diameter smaller than that of the first driving submodule. This plunger is loaded with spring 432, such that the default position of the small tube's plug is near its lower end (i.e. proximate to structural submodule 460). Similar to the fluid dynamics described in the "Squeeze" configuration, the motion of this plug can create a low pressure in the smaller tube, which pulls smoke from the combusting material (prepackaged 752 or loose) into its internal volume. Depressing the plunger again, then, ejects the smoke through the inhalation aperture 240 on the standard cap module 410.

Subcomponents of the "pipette" inhalation device configuration include: the plunger 434, a first driving submodule 430 (for example, a plunger tube), plunger 451 sans shaft, a second driving submodule 450 (for example, a plug tube), flexible tube 442 (for example, a u-bend tube), spring 432, and a frame including a docking submodule 420 and a structural submodule 460. The frame (420 and 460) holds both plunger tube and plug tube in place, also providing a level of impact resistance for the device. Additionally, this frame contains two magnets 423 oriented such that the standard cap module 410 releasably affixes to the frame and is thus, in fluid communication with the internal volume of the second driving submodule (e.g. plug tube) 450. The plug tube is where smoke from combusting material (whether prepackaged 752 or loose) enters ingress tube 421 and exits egress tube 422, each disposed through the docking submodule 420, as the plug expands and contracts this enclosed volume, respectively. The plug itself 451 is the intersection between open volume and a hydraulic fluid 441 (e.g. water or another incompressible fluid) sections of the plug tube. This plug slides vertically within the plug tube as the fluid (translating the force from the plunger 434) exerts a push or pull upon it. The spring 432 resides between the button 431 end of the plunger and the frame. It serves to establish a default position of the plunger 451 (and therefore the plug 451 to which it is hydraulically coupled).

The "Venturi" configuration consists essentially of an enclosed loop 530. Within this loop, either an impeller or propeller 544 (which is coupled to a motor 541 via a watertight gear shaft 542) induces the flow of water. The interior of the loop has two features which break with its otherwise constant diameter circular tube geometry. First, a gradual constriction of the tube (with a t-intersection leading away from the enclosed loop 530) serves as a venturi valve. When the standard cap module 510 is placed atop the venturi device, the bowl 221 is connected to this constriction 531 via an ingress tube 521. Thus, as the water is being pumped through the main loop, the low pressure generated by the venturi effect pulls bubbles of air (or smoke from prepackaged 752 or loose combusting material) into the fluid flow. The other feature of this main loop is a bulb 532, located opposite the venturi valve portion of the loop. This bulb allows for the bubbles of smoke being pulled in by the venturi effect to collect in a volume not occupied by the flowing water. Once the prepackaged or loose material is fully combusted, and the smoke has collected in the bulb feature, the user may inhale this smoke through the cap module's inhalation aperture 240. The cap module's inhalation aperture 240 is connected to this bulb via an egress tube 522 similar to that which connects the cap module's recess aperture with the venturi constriction feature.

Subcomponents of the "venturi" configuration include the enclosed loop 530, the handle tubes, for example, ingress tube 521 and egress tube 522, the impeller (or propeller) 544, and the motor 541. As with the other configurations, docking submodule 520 contains a pair of magnets 523 oriented such that the standard cap module 510 releasably affixes to the docking submodule and is thus, in fluid communication with the internal volume of primarily circular cross section comprising the enclosed loop 530. Additionally, the removable cap module 510 will serve as the intake and outtake points for the system. The motor, activated by a simple switch, is coupled with the impeller (or propeller), driving its rotation, which in turn causes the water inside the main tube to flow at a constant rate. The handle tubes serve to connect the bulb 532 (for collecting smoke bubbles) comprising a bulbous volume and the gradual constriction, for example venturi valve, 531 (for pulling in smoke bubbles) to the docking submodule (e.g. cap module port) 520 configured to receive the cap module 510. In an embodiment, a yoke 545 releasably affixes the motor 541 to the enclosed loop 530 structure. In another embodiment, a ninety degree gear transmission (e.g. bevel gearbox, flexible gear shaft, etc.) 543 may be configured to rotate the gear shaft 542 using the motor 541.

The "Lever" configuration consists of a body chamber 640 that fits into a base submodule 650 that has a hole 641 therein. The lever 631 is spring-loaded (via torsion spring 633 captured by axle 635, about which the torsion spring 633 pivots, and located largely within recess 634), thus sealing this hole by default. The user may fill the device with water, replacing its top 620 (and standard cap module 610) before squeezing the lever 631 to allow said water to exit the internal volume. The water draining from the internal volume (into a sink, onto the ground, etc.) creates a low pressure, which in turn pulls in the smoke of combusting loose or prepackaged 752 material from the bowl 221 in the standard cap module. Once the water has drained from the device, the user may inhale the resultant packet of smoke from the cap module's inhalation aperture 240 (keeping the lever squeezed so that air may enter in order to replace that being inhaled by the user). The lever itself is affixed to a base cap 650, which also serves to stabilize the device when standing upright on a flat surface.

Subcomponents of the "lever" configuration include the lever 631, the body chamber 640, the top 620, the base submodule 650, the lever axle 632, and the torsion spring 633. As is the case with other devices, this configuration requires a standard, releasably connected cap module 610 as well. The lever 631 is mounted on the lever axle 632 about which the lever 631 pivots, and is held against the base submodule 650 by the torsion spring 633. The top cap fits over the glass, and the base submodule has a hole (creating a constant diameter path for water to exit the glass once the lever is pulled). As with the other configurations, an ingress tube 621 and an egress tube 622 are disposed through a docking submodule 620 (for example, the top 620), and they correspond with ingress tube 220 and the egress tube 240 of the standard cap module, respectively. A pair of magnets 623 corresponds with the pair of magnets 231 of the standard cap module.

Additional and alternative configurations of the inhalation device are possible. Magnetic, gravitational, centrifugal, hydraulic, pneumatic, and other forces may be employed to directly or indirectly engender the low pressure necessary for the ingress of combusting material (prepackaged or loose). Each inhalation device base functions with the standard cap module, allowing for standardized prepackaged combustible material insertion, and ultimately, smoke inhalation.

Prepackaged combustible material includes a combustible package and a predetermined amount of a combustible material. Combustible packaging is preferentially comprised of leaves, either in whole or processed (i.e. paper sheet) form. Various shapes of combustible packaging are possible. A single serve combustible package may be a pill-shape (i.e. oblong) capsule, octagonal prism, heptagonal prism, hexagonal prism, pentagonal prism, rectangular prism, triangular prism, cylinder, sphere, tetrahedron, rhombic dodecahedron, truncated octahedron, droplet or pouch. Materials which comprise a unit include a combustible wrapper which delimits a unit's external volume, and combustible material enclosed within said volume. The combustible material may be ground, chopped, shredded, powdered, foamed, crystalline, or whole. Combustible material may include cannabis, marijuana, tobacco, salvia, catnip, or any other (preferably plant-based) active substance. This may entail ground leaves, flowers, or processed derivatives thereof.

The combustible packaging itself is preferably a sheet created by the processing of leaves. This sheet material, when wet, is pliant, such that it may assume the shape of a mold under mild force. The combustible material contained therein (i.e. active substance) is comprised of many small pieces, no larger than 5 mm along any dimension, and typically much smaller than that. This sizing may be achieved by chopping, grinding, or shredding leaves and/or flowers. Alternately, if derivatives constitute a whole or part of the enclosed combustible material, they may be powdered, foamed, crystalline, or whole when they are enclosed by the combustible packaging material during the manufacturing process.

A "Kit" generally includes an inhalation device and instructions for the use thereof.

The instructions of a kit may direct a user to: (optionally) assemble the inhalation device from its constituent parts; fill a specific section of the device with water; place one unit of prepackaged combustible material (or loose material) into the bowl of the cap; place the cap onto its port atop the device (using the magnets to confirm orientation); "activate" the device, either by pressing a button, pulling a lever, squeezing a bulb, etc. (depending on the embodiment of the inhalation device); hold a flame to the prepackaged or loose material; after observing the prepackaged or loose material combust fully, inhale the smoke through the cap's slot (aka "inhalation aperture"). This final step may be coincide with a continued "activation" of the device (i.e. lever pull, button press, hand squeeze, etc.), in order to equalize pressure in the chamber from which smoke is being inhaled.

The kit may further include at least one unit of prepackaged combustible material.

Generally, the method of making prepackaged combustible material entails three primary stages: creating and shaping the combustible material packaging, placing the combustible material within the combustible packaging, and sealing the combustible packaging around the combustible material. This may be done at the scale of one prepackaged unit at a time as illustrated in FIG. 7, or en mass (i.e. 1000+ units per sheet) as illustrated in FIG. 8.

As shown in FIG. 7, an intact leaf 711 may be processed or destemmed to yield a destemmed leaf 712 and then steamed using a surface comprised of small holes 722, distributing steam evenly across the entirety of a two dimensional, a flat, waterproof and heat-proof surface 723. Thereafter, the steamed sheet is pressed into a female mold 732 by a corresponding male mold 731. This may be done at the scale of one prepackaged unit at a time as illustrated in FIG. 7. A small hole 733 extending from the base of the female mold interior to the exterior surface of the female mold structure receives a hollow tube 741, which delivers ground (or chopped, shredded, powdered, foamed, crystalline, or whole) combustible material. A crimping machine 751 is used to enclose a single single-serve, prepackaged combustible material unit 752. A rotationally movable structure 760 is configured to rotate the prepackaged combustible material unit 752 and a translationally moveable structure 771 is configured to move the prepackaged material unit 752 in a sideways or up-and-down direction as needed for the making of the prepackaged combustible material unit 781. Additionally, a purch or pin 772 nominally smaller than the corresponding hole in the female mold (illustrated in FIG. 11 in its inverted orientation) is used to aide the release of the completed prepackaged combustible material unit 781 from the female mold (to be optionally further processed into secondary (e.g., packages of 20), tertiary (e.g., cartons of a dozen packages), and quaternary (e.g., boxes of 10 cartons) packaging. In an embodiment, the prepackaged combustible material has a weight of about 1.5, 1.4, 1.3, 1.2, 1.1, 1.0, 0.9, 0.8, 0.7, 0.6, 0.5, 0.4, 0.3, 0.2, or 0.1 grams.

Figure 8:
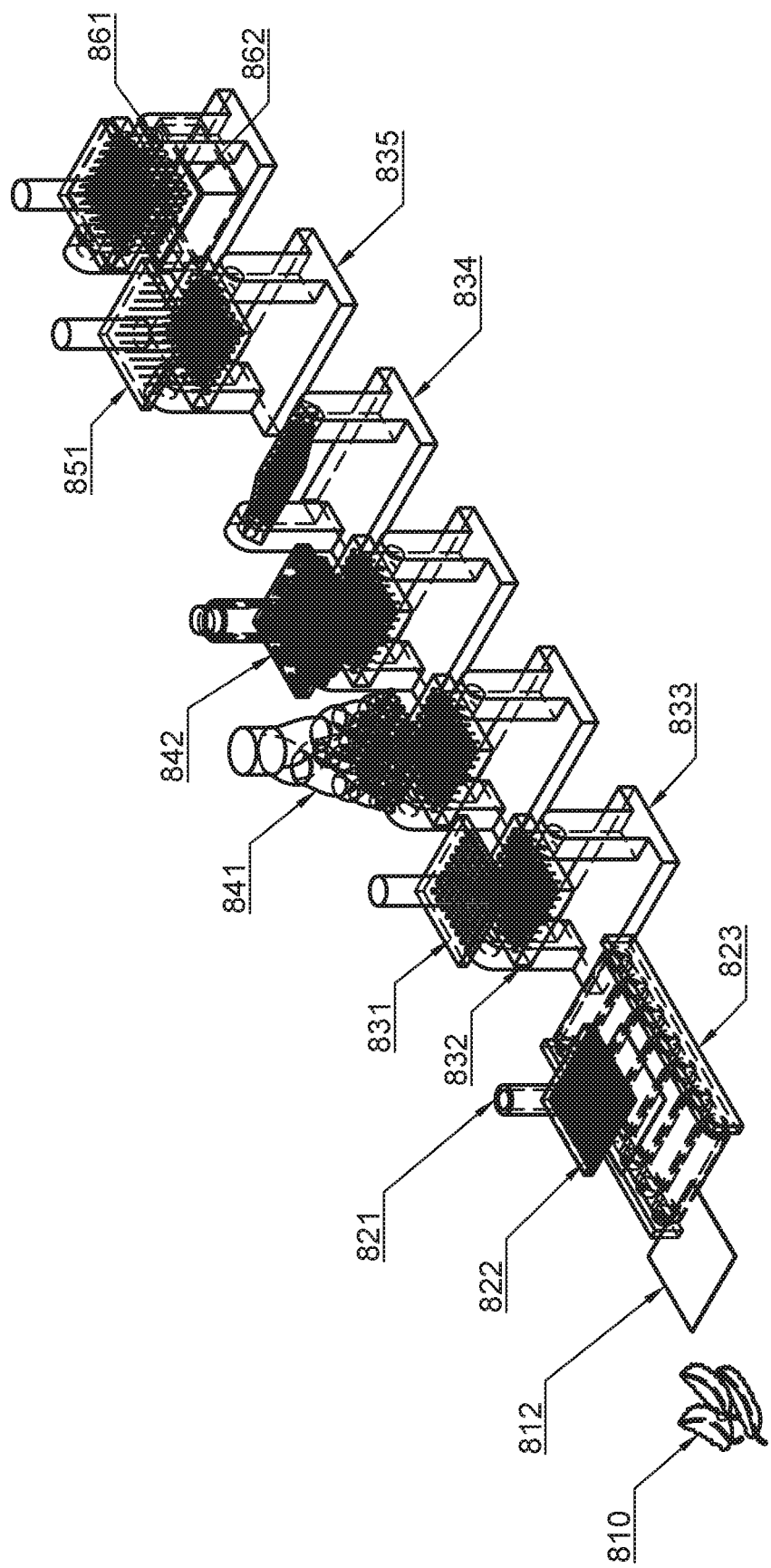
FIG. 8 illustrates a system for making prepackaged combustible, single-serving material units on a commercial scale, according to another embodiment of this disclosure.
Figure 8A:
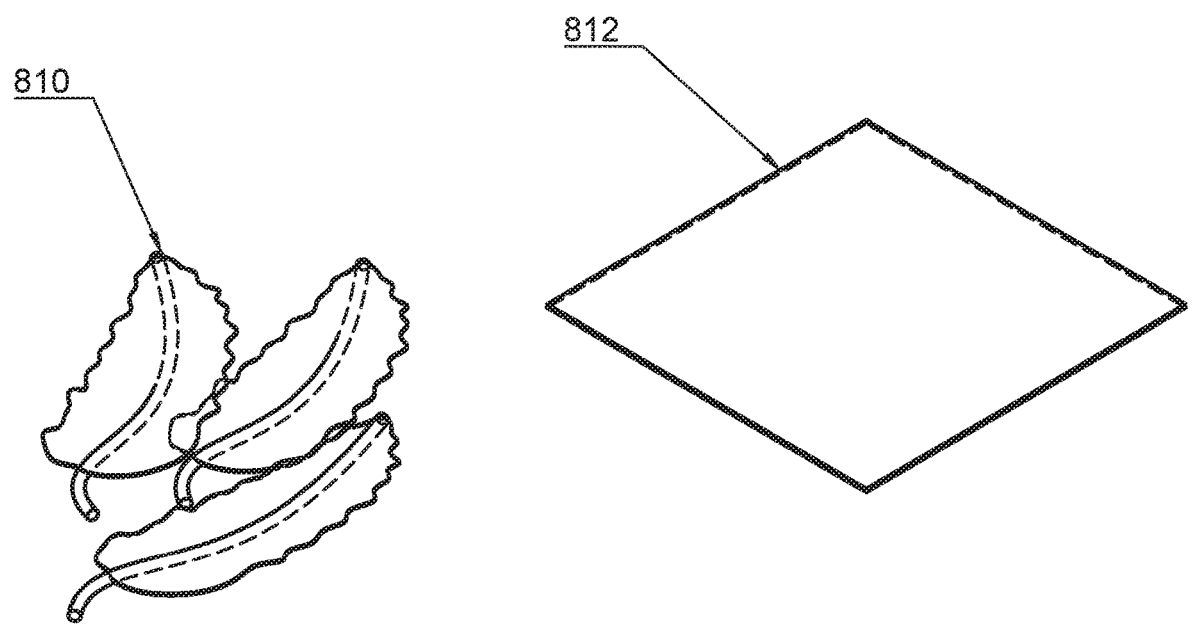
FIG. 8A illustrates an enlarged view of first and second elements of the system shown in FIG. 8, according to an embodiment of this disclosure.
Figure 8B:
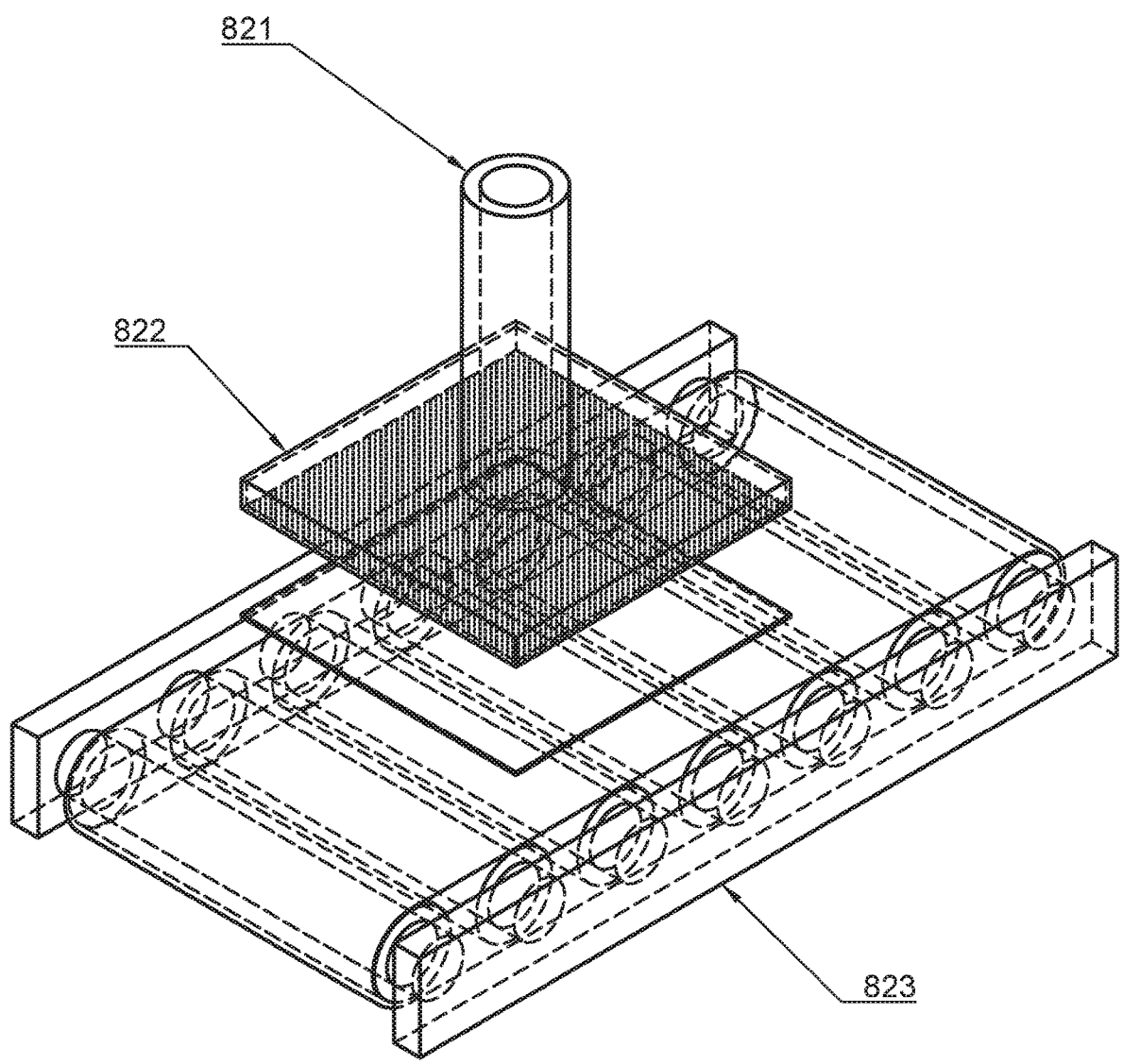
FIG. 8B illustrates an enlarged view of the first and second elements of the system shown in FIG. 8, according to an embodiment of this disclosure.
Figure 8C:
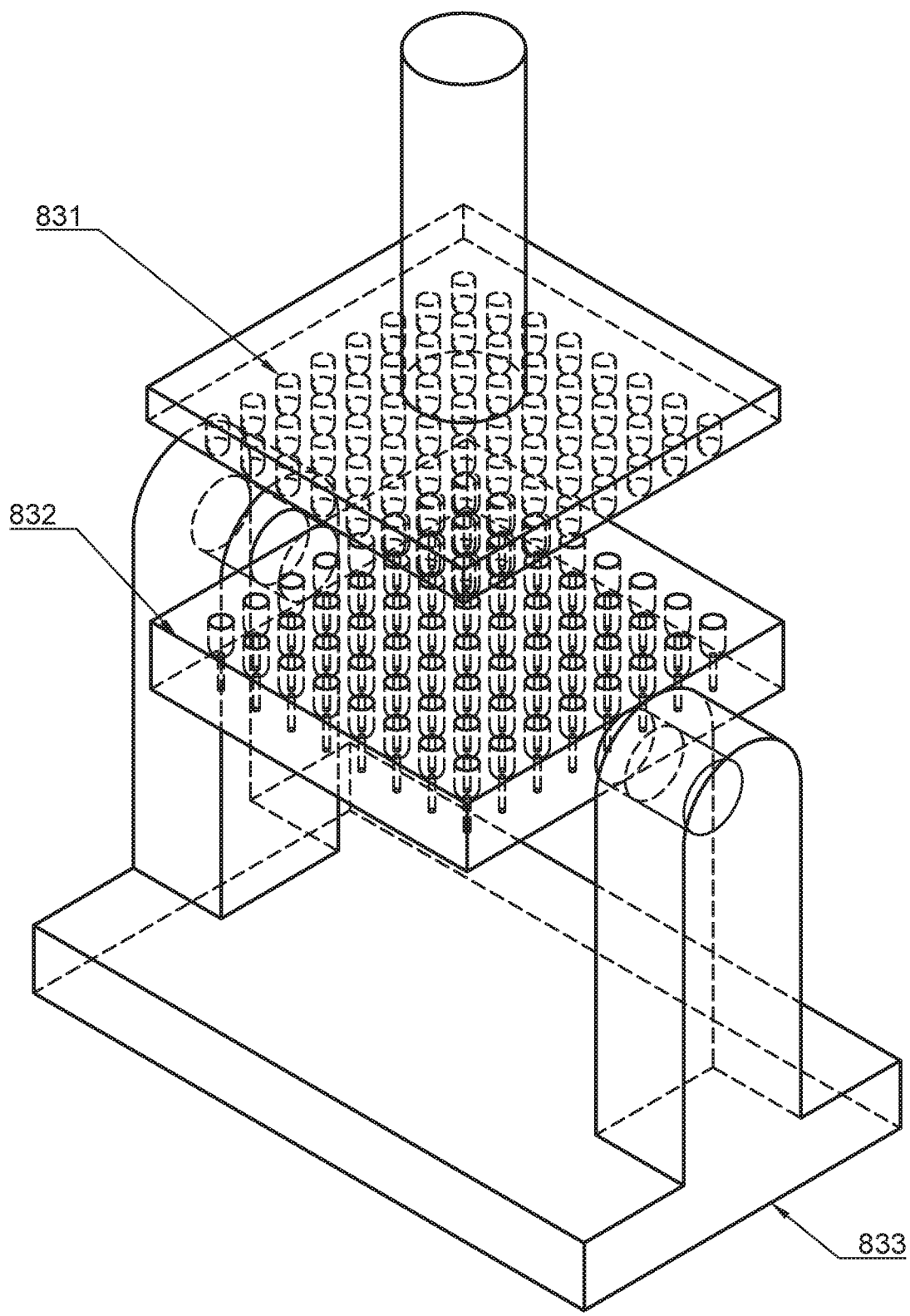
FIG. 8C illustrates an enlarged view of the third element of the system shown in FIG. 8, according to an embodiment of this disclosure.

FIG. 8 illustrates a system for making single-serve prepackaged combustible material units on a commercial scale. FIGS. 8A-8H illustrate the individual parts of the system shown in FIG. 8. As shown in FIG. 8A, to create combustible material packaging en mass (i.e. 1000+ units per sheet), leaves or plant fibers 810 are processed into fibrous sheet form 812. In an optional embodiment, the leaves or plant fibers of 810 comprise destemmed leaves of a same species of material as that contained within the prepackaged material units formed in FIG. 7. As illustrated in FIG. 8B, fibrous sheet 812 is moved by a conveyor belt 823 and then steamed (via steam tube 821 and using diffusor plate 822). In an embodiment, diffusor plate 822 is a two dimensional surface comprised of small holes, distributing the steam evenly across the entirety of the two dimensional surface. Referring to 8C, the steamed material is subsequently shaped by being pressed into a female mold 832 by a corresponding male mold 831 using a rotationally movable support 833 for the female mold assembly 832.

Figure 8D:
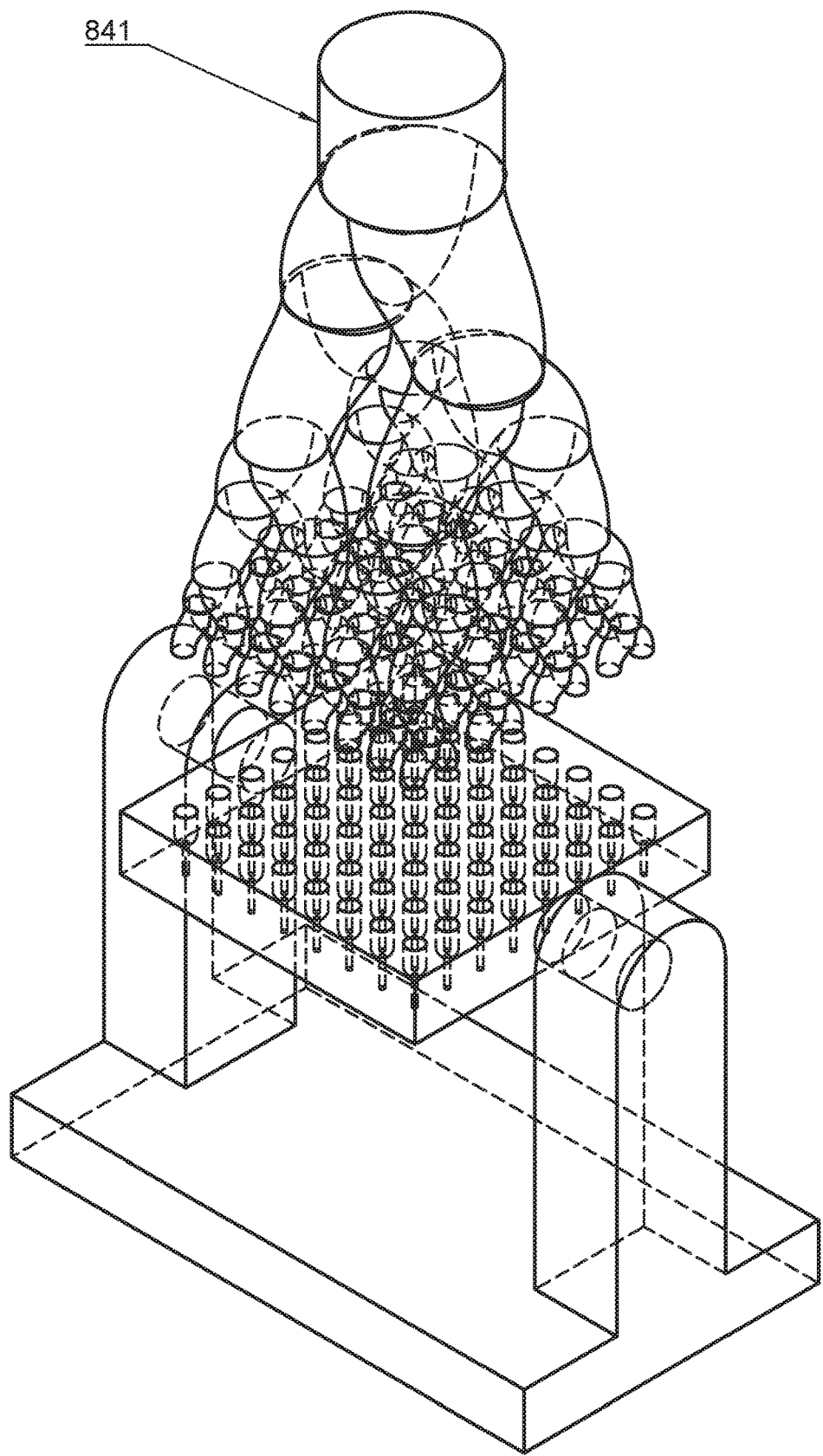
FIG. 8D illustrates an enlarged view of the fourth element of the system shown in FIG. 8, according to an embodiment of this disclosure.
Figure 8E:
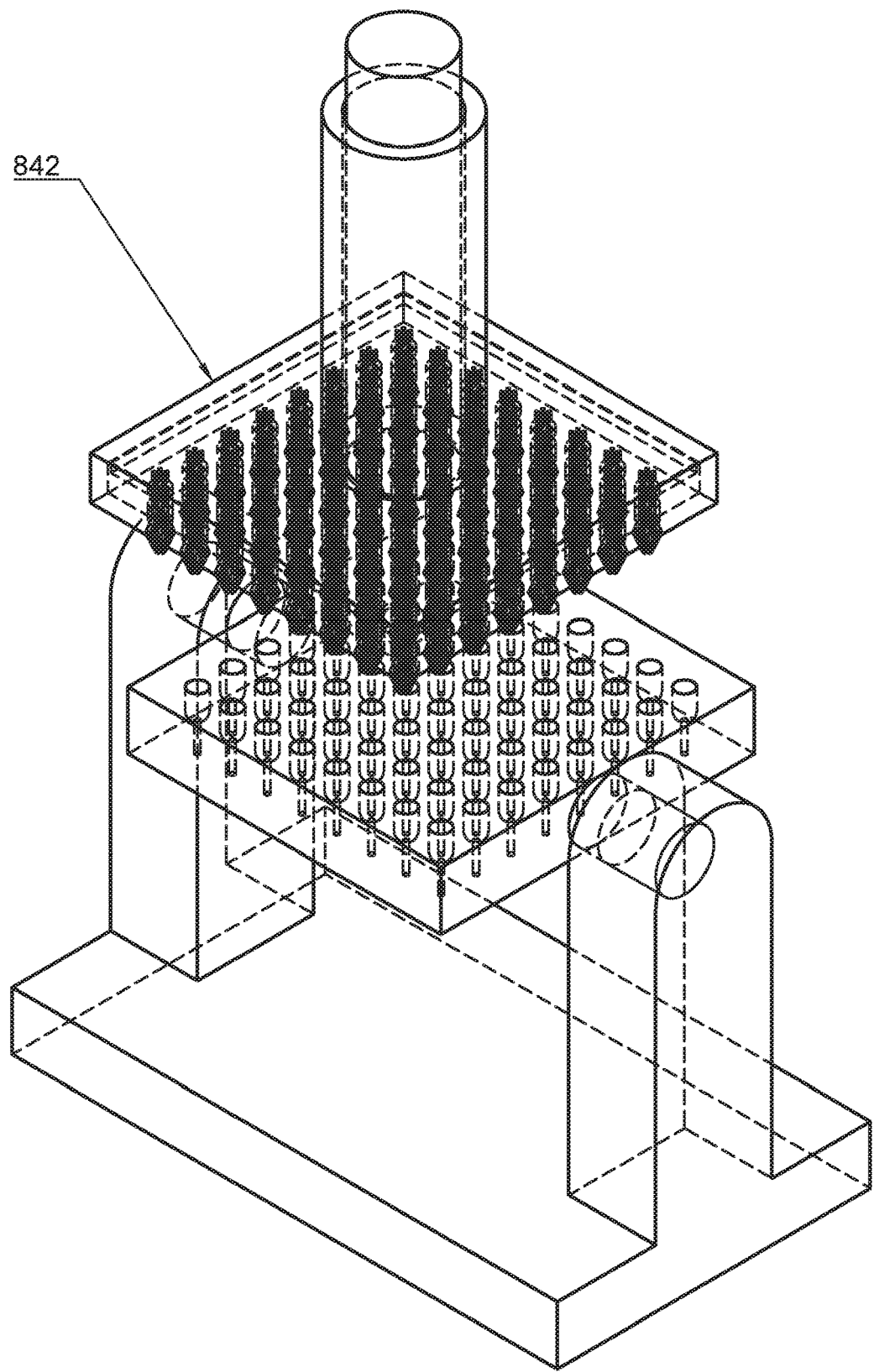
FIG. 8E illustrates an enlarged view of the fifth element of the system shown in FIG. 8, according to an embodiment of this disclosure.
Figure 8F:
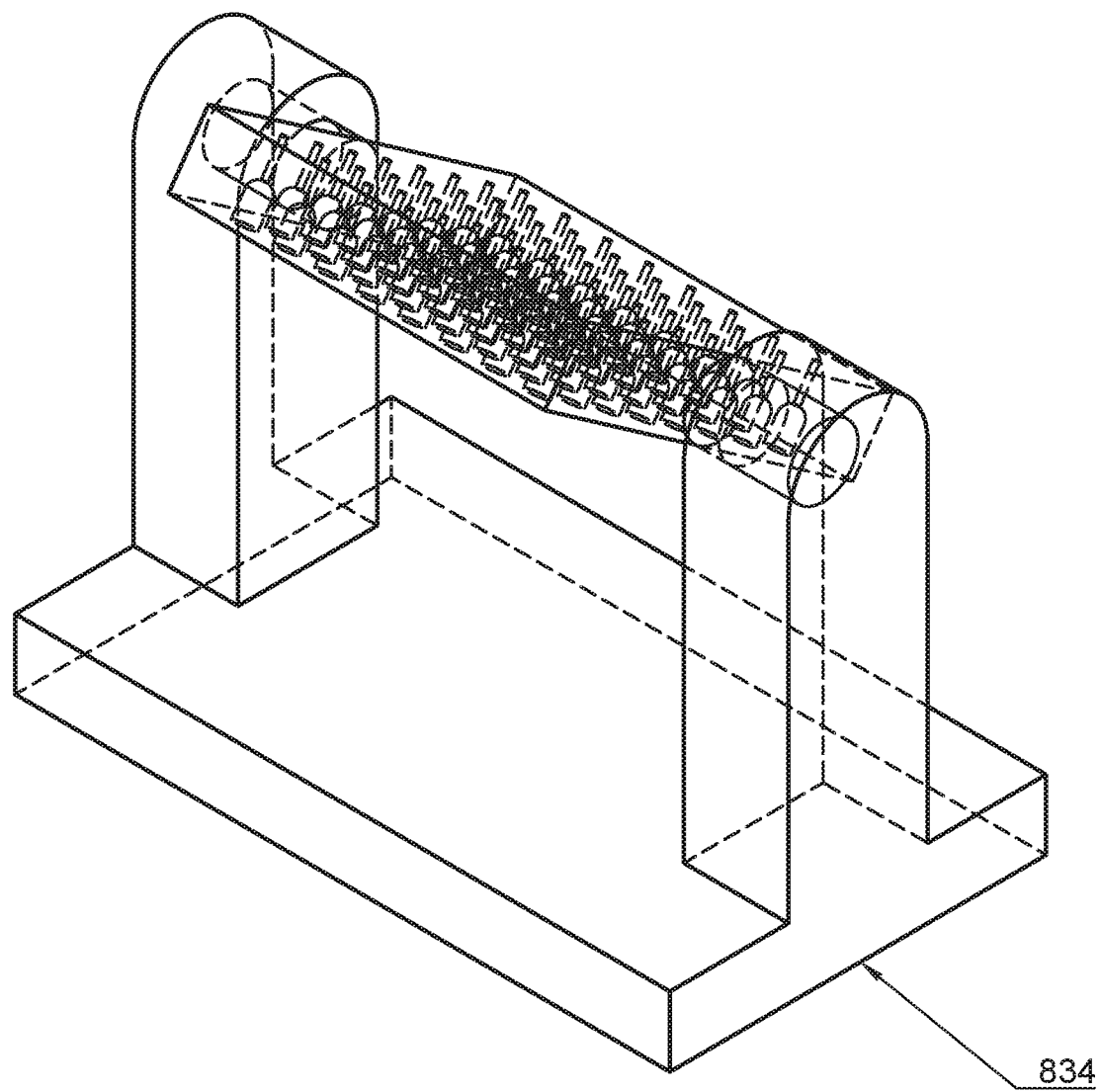
FIG. 8F illustrates an enlarged view of the sixth element of the system shown in FIG. 8, according to an embodiment of this disclosure.
Figure 8G:
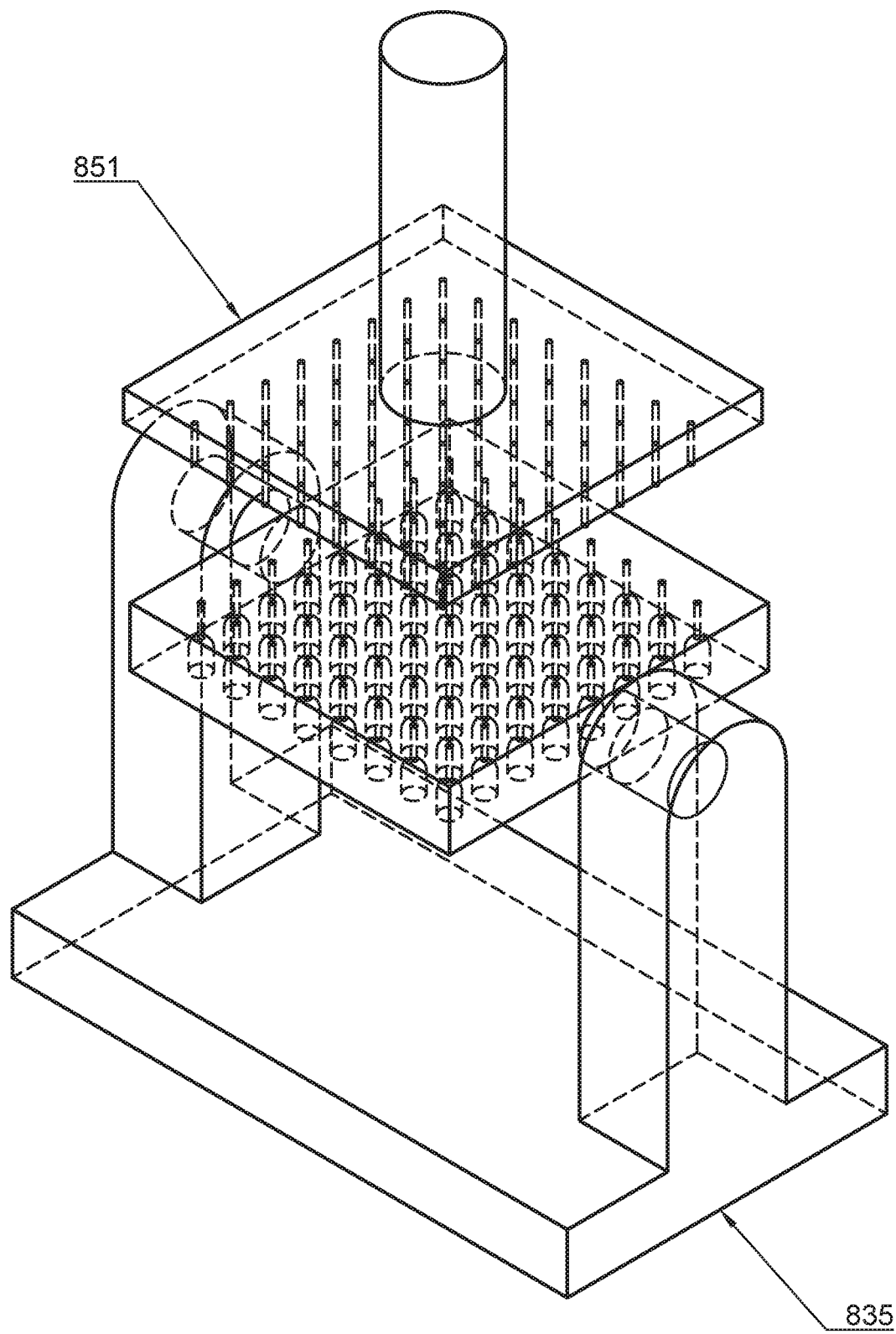
FIG. 8G illustrates an enlarged view of the seventh element of the system shown in FIG. 8, according to an embodiment of this disclosure.
Figure 8H:
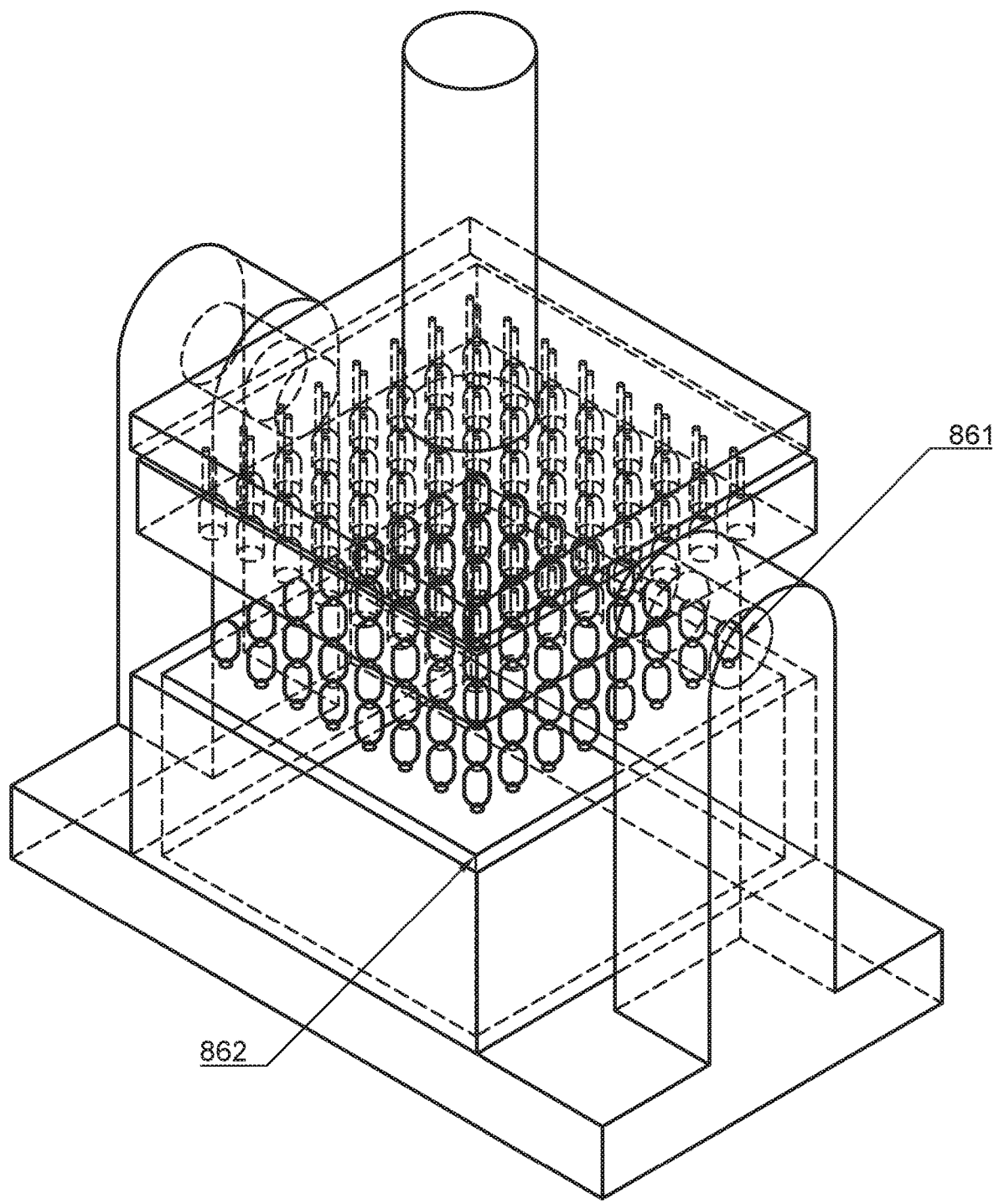
FIG. 8H illustrates an enlarged view of the eighth element of the system shown in FIG. 8, according to an embodiment of this disclosure.

Once the sheet material is pressed into shape, the shaped material is filled with small granules (also referred to herein as particulate material or particulates) of combustible material, dispensed from a branching structure 841 as illustrated in FIG. 8D. In various embodiments, the branching structure 841 may comprise one of a branched manifold, a granular conveyance, a feed manifold, or a branched structure. After filling, an area (e.g. circle) surrounding the opening of each unit is sliced, or separated from the surrounding sheet material. This flap of material is then pinched together and crimped by a crimping machine 842, shown in FIG. 8E. The crimping machine 842 seals the combustible material inside a combustible packaging and forms the combustible prepackaged units 861 (also referred to herein as a nano-joint) as shown in final form in FIG. 8H. After the crimping machine seals the combustible prepackaged units, the rotationally movable structure 833, for example a mold structure 832, holding these combustible prepackaged unit(s) 861 is flipped upside down. FIG. 8F illustrates the support 833 at mid rotation position 834. Once the rotationally movable structure 833 is inverted 180 degrees as shown in FIG. 8G at reference numeral 835, a set of pins 851 is inserted into the back end of the mold. Each of the pins in the set of pins 851 contacts a corresponding prepackaged unit 861, bringing the prepackaged combustible units out of the mold releasing them onto a conveyor, container 862, or other transport mechanism to be further processed. FIG. 8H illustrates the prepackaged combustible units 861 and container 862 positioned to receive the prepackaged combustible units when released. Namely, as with the embodiments illustrated in FIG. 7, they may be arranged and enclosed further through secondary (e.g., packages of 20), tertiary (e.g., cartons of a dozen packages), and quaternary (e.g., boxes of 10 cartons) packaging.

The disclosed systems provide a mechanized, replicable process for producing a defined and consistent quantity of smoke (e.g., a measured or metered dose) from, for example, either loose or prepackaged combustible material. As such, each embodiment of the device is operated differently, but all are activated using only the force and dexterity afforded by one hand. Once the device is activated, a certain period of time passes before the material (again, loose or prepackaged) has fully combusted. At this time, the user may inhale the smoke through the inhalation aperture on the standard cap module. While inhaling, each device requires the user's continued activation (in order to equalize pressure within the device's closed volume).

In an embodiment, a method of using a system including the "hourglass" inhalation device includes: First, fill one chamber of the device with water. Place the standard cap module atop the device (using the magnets' orientation to confirm proper placement) and fill the recess with loose or prepackaged combustible material. In order to activate the device, depress the button while igniting the combustible material in the recess (with a lighter, match, etc.). Continue to press the button while the water falls from the upper to lower chamber. During this period, the combustible material should stay lit. Once the water has fallen, the upper chamber should be full of smoke. To clear the chamber, place your lips on the cap module edge (i.e. inhalation aperture) and inhale, while still pulling the button. If desired, remove the cap module, flip the entire device over, and repeat the process.

In another embodiment, a method of using a system including the "squeeze" inhalation device includes: Fill the recess of a standard cap module with loose or prepackaged combustible material. Place the cap module atop the squeeze device, using the magnets to ensure proper orientation. Then, squeeze the bulb, causing the plug to rise towards the cap module. At this point, ignite the combustible material while slowly unsqueezing the bulb. The plug will recede back towards the bulb, pulling smoke into the chamber as is does so. Once the plug has returned to its original position, place your lips on the straw (i.e. inhalation aperture) and inhale, squeezing the bulb again as you do so.

In yet another embodiment, a method of using a system having a "pipette" inhalation device includes: Fill the recess of a standard cap module with loose or prepackaged combustible material. Place the cap module atop the pipette device, using the magnets to ensure proper orientation. Then, depress the button with your thumb, causing the plug to rise towards the cap module. Once it has reached its apex, ignite the loose or prepackaged combustible material while slowly releasing pressure on the button. The plug will recede, pulling smoke into the chamber. When the button has returned to its original position, and the material has combusted fully, place your lips on the slot (i.e. inhalation aperture) and inhale, pressing the button again as you do so.

In an embodiment, a method of using a system having a "venturi" inhalation device includes: First, fill the venturi device with water. Then, turn on the motor to start pumping the water around the loop. Once the water has reached a constant looping speed, fill the recess of a standard cap module with loose or prepackaged combustible material and place the cap module atop the venturi device, using the magnets to ensure proper orientation. Ignite the loose or prepackaged combustible material, and allow to fully combust before turning off the motor. At this point, place your lips on the slot (i.e. inhalation aperture) and inhale.

In another embodiment, a method of using a system having a "lever" inhalation device—First, remove the top cap. After filling the device with water, replace the top cap, and place a standard cap module atop that (using the magnets to confirm orientation). Fill the recess with loose or prepackaged combustible material. Then, holding the device over a sink, outdoors, or otherwise waterproof environment, squeeze the lever and ignite the prepackaged or loose combustible material. Once the water has drained completely, place your lips on the edge of the cap module (i.e. inhalation aperture) and inhale, continuing to squeeze the lever as you do so.

As a system which creates a replicable, defined quantity of smoke (e.g., a measured or metered dose), the disclosed systems are suitable in various medical or therapeutic treatment regimens and/or for recreational use. For example, the disclosed systems, devices, and methods may be employed to deliver a known, consistent dose of one or more active substances to a patient or other user who has been prescribed or otherwise wishes to inhale that active substance.

The following description provides an overview of the figures and the various reference numerals included therein beginning at FIG. 1A(i) through FIG. 8. FIGS. 1A(i), 1A(ii), 1B, and 1C illustrate an "hourglass" style inhalation device, according to an embodiment disclosed herein. Reference number 110 is a standard cap module as further described in reference to FIG. 2. Reference number 120 is a valve body. Reference number 121 is a valve plunger. Reference number 131 is an ingress tube. Reference number 132 is an egress tube. Reference number 133 is a sleeve (i.e. a soft layer between the ingress/egress tubes and the valve body). Reference number 140 is a docking submodule. Reference number 141 is a pair of magnets (the polarity of each magnet of the pair of magnets is aligned in order to receive the standard cap module). Reference number 142 is a flanged sleeve (providing a soft interface between the docking/structural submodule and the body chamber). Reference number 143 is another flanged sleeve (providing a soft interface between the body chamber and the center block). Reference number 144 is a center block. Reference number 145 is a constriction with approximately a circular cross section. Reference number 146 is a ball bearing. Reference number 147 is a bowl for loose or prepackaged combustible material. Reference number 148 is a structural submodule with integrated ingress and egress structures. Reference number 150 is a body chamber (for example, the "top" chamber in this orientation or embodiment). Reference number 151 is another body chamber (for example, the "bottom" chamber in this orientation). Reference 160 is a button shaft. Reference number 161 is a series of apertures (serving to permit fluid communication between the bottom body chamber and the ambient atmosphere). Reference number 162 is a double plunger. Reference number 163 is an o-ring (serving as the interface between the button shaft 160 and button sheath 165). Reference number 164 is a groove (sized to securely, yet releasably hold the o-ring). Reference number 165 is a button sheath. Reference number 166 is a screw (which threads into the button sheath). Reference number 167 is a nub (for tactile and decorative effect). Reference number 181 is an aperture leading to the recess in which the button resides. Reference number 182 is another aperture leading to the recess in which the button resides.

FIG. 2 illustrates the standard cap module, for use with any inhalation device base. Reference number 220 is an ingress tube of the cap module. Reference number 221 is a bowl (for loose or prepackaged combustible material. Reference number 222 is a constriction with approximately circular cross section. Reference number 230 is a cap module body. Reference number 231 is a pair of magnets (whose polarity are aligned in order to receive the standard cap module. Reference number 240 is an inhalation aperture. Reference number 241 is a spherical bearing. Reference number 242 is a washer having an inner diameter slightly smaller than the outer diameter of the spherical bearing. Reference number 243 is an aperture with diameter approximately equal to that of the washer's exterior.

Figure 3A:
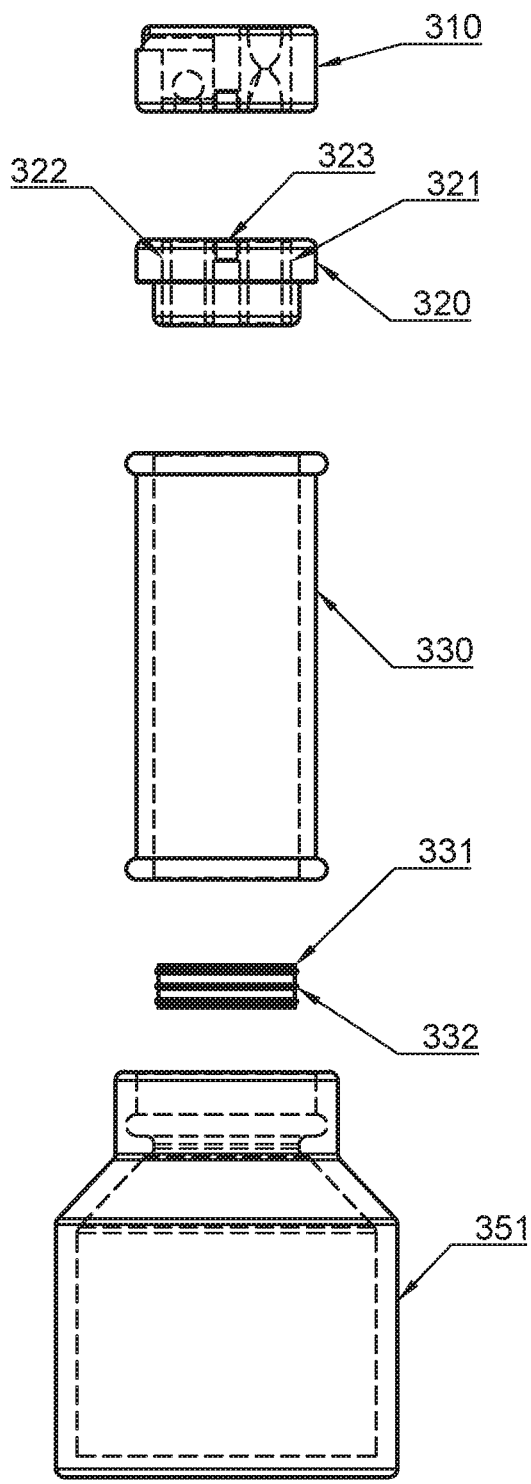
FIG. 3A(i) illustrates a side view of a "squeeze" style inhalation device, according to an embodiment of this disclosure.
Figure 3B:
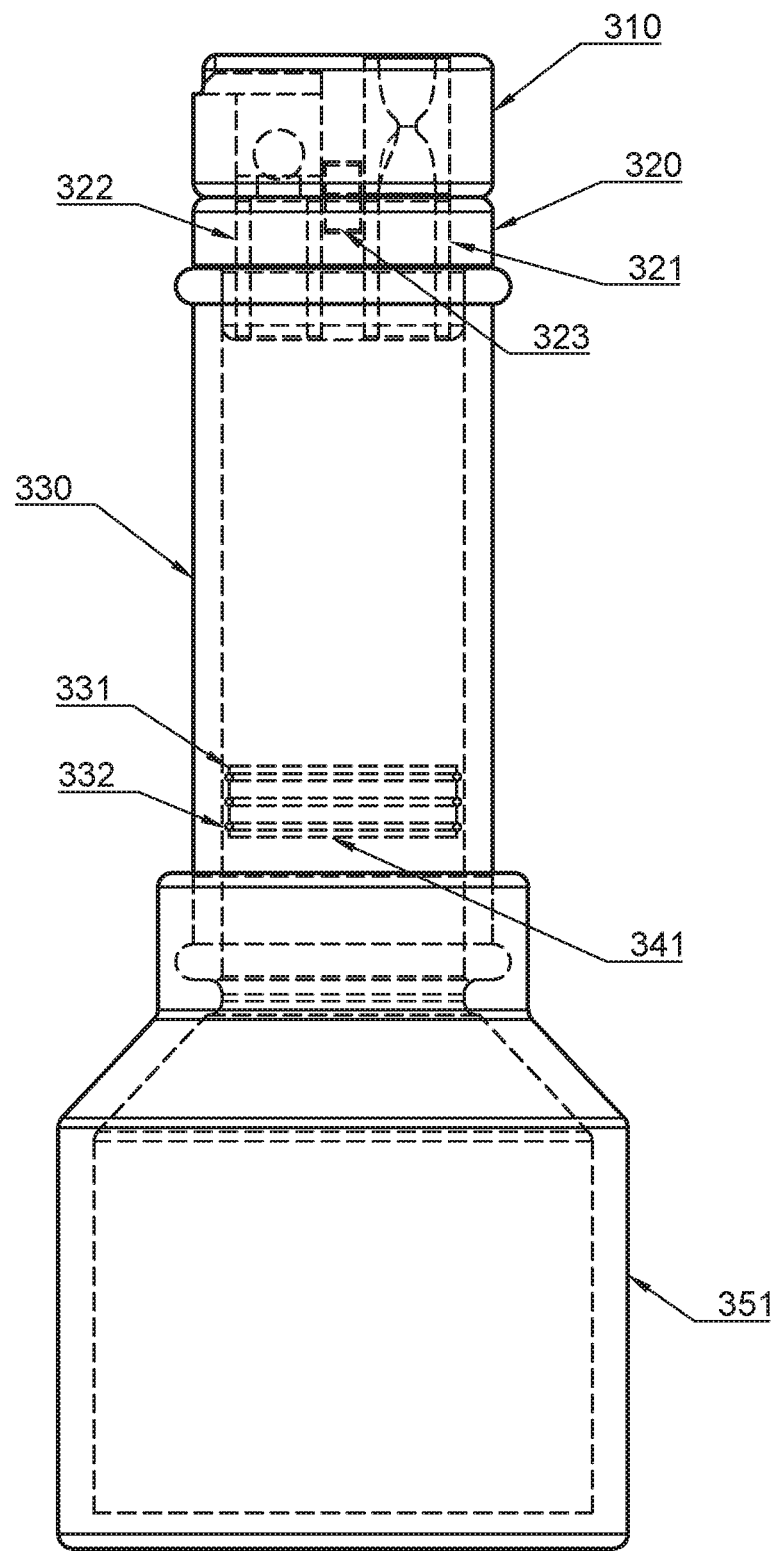
FIG. 3B illustrates a side view of a "squeeze" style inhalation device in an assembled position, according to an embodiment of this disclosure.

FIGS. 3A(i), 3A(ii), and 3B illustrate a "squeeze" style inhalation device according to an embodiment disclosed herein. Here, reference number 310 is a standard cap module (as described in relation to FIG. 2). Reference number 320 is a top or docking submodule (to receive a standard cap module). Reference number 321 is an ingress tube through the docking submodule. Reference number 322 is an egress tube through the docking submodule. Reference number 323 is a pair of magnets (whose polarity are aligned in order to receive the standard cap module). Reference number 330 is a tube. Reference number 331 is a plug. Reference number 332 is an o-ring. Reference number 341 is an incompressible fluid (e.g. water). Reference number 351 is an elastically compressible bulb.

FIGS. 4A, 4B(i), and 4B(ii) illustrate a "pipette" style inhalation device according to an embodiment disclosed herein. Reference number 410 is a standard cap module (as described relative to FIG. 2). Reference number 420 is a docking (and structural) submodule. Reference number 421 is an ingress tube through said docking/structural submodule. Reference number 422 is an egress tube through said docking/structural submodule. Reference number 423 is a pair of magnets (whose polarity are aligned in order to receive the standard cap module). Reference number 430 is a first driving submodule. Reference number 431 is a button. Reference number 432 is a spring. Reference number 433 is a plunger shaft. Reference number 434 is a plunger. Reference number 435 is an o-ring. Reference number 441 is an incompressible fluid (e.g. water). Reference number 442 is a tube connecting the first driving submodule and the second driving submodule chambers. Reference number 450 is a second driving submodule (also referred to herein as a driven submodule). Reference number 451 is a plunger (sans shaft). Reference number 452 is another o-ring. Reference number 460 is a structural submodule.

FIG. 5 illustrates a "venturi" style inhalation device, according to an embodiment disclosed herein. Reference number 510 is a standard cap module (as described in FIG. 2). Reference number 520 is a docking submodule (to receive a standard cap module). Reference number 521 is an ingress tube through said docking submodule. Reference number 522 is an egress tube through said docking submodule. Reference number 523 is a pair of magnets (whose polarity are aligned in order to receive the standard cap module). Reference number 530 is an internal volume of primarily circular cross section comprising a loop. Reference number 531 is constriction of approximately circular cross section (i.e. a venturi valve). Reference number 532 is a bulbous volume. Reference number 541 is a motor. Reference number 542 is a gear shaft extending from said motor. Reference number 543 is a ninety degree gear transmission (e.g. bevel gearbox, flexible gear shaft, etc.). Reference number 544 is, optionally, an impeller or propeller. Reference number 545 is a yoke, releasably affixing the motor to the loop structure.

Figure 6A:
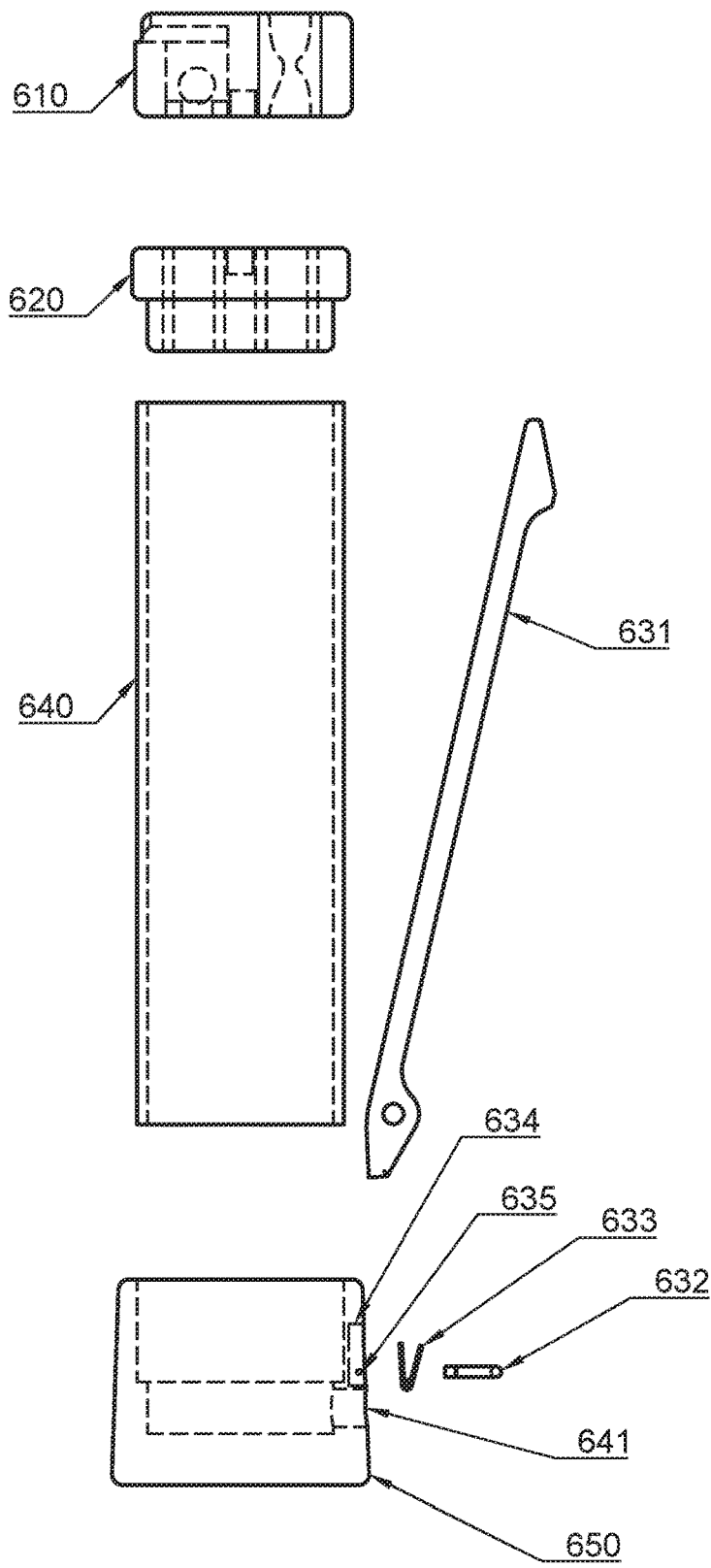
FIG. 6A(i) illustrates an exploded side view of the parts of a "lever" style inhalation device, according to an embodiment of this disclosure.
Figure 6B:
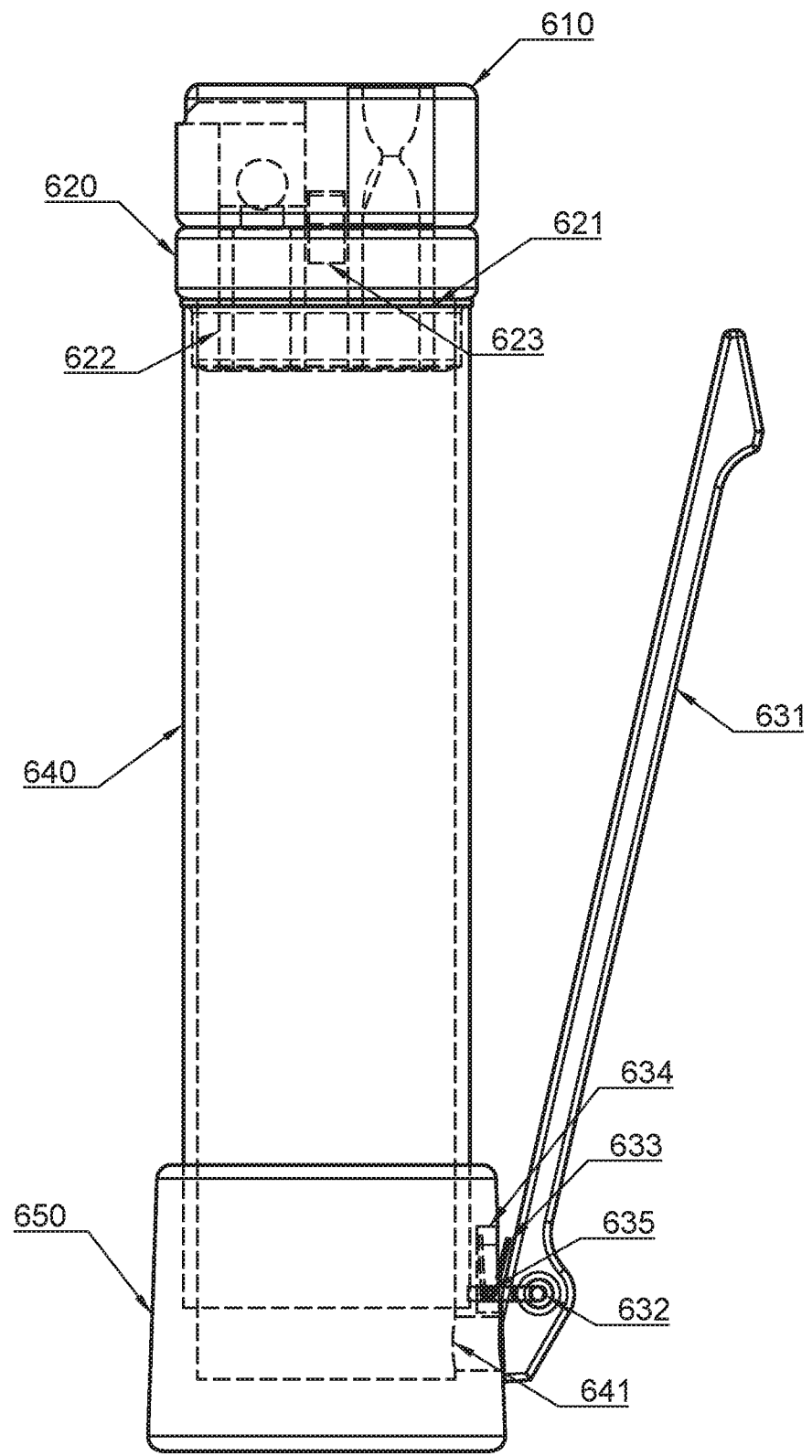
FIG. 6B illustrates a side view of a "lever" style inhalation device in an assembled position, according to an embodiment of this disclosure.

FIGS. 6A(i), 6A(ii), and 6B illustrate a "lever" style inhalation device, according to an embodiment disclosed herein. Reference number 610 is a standard cap module (as described in relation to FIG. 9). Reference number 620 is a top (to receive a standard cap module). Reference number 621 is an ingress tube through said docking submodule. Reference number 622 is an egress tube through said docking submodule. Reference number 623 is a pair of magnets (each of the pair having a polarity that is aligned in order to receive the standard cap module). Reference number 631 is a lever. Reference number 632 is an axle, about which the lever pivots. Reference number 633 is a torsion spring. Reference number 634 is a recess, housing said torsion spring. Reference number 635 is an axle, about which the torsion spring pivots. Reference number 640 is the body chamber. Reference number 641 is a hole in the base submodule. Reference number 650 is a base submodule.

FIG. 7 illustrates a method of making prepackaged combustible material (as single units, for visual clarity). Reference number 711 is an intact leaf. Reference number 712 is a destemmed leaf. Reference number 722 is a surface comprised of small holes, distributing steam evenly across the entirety of the two dimensional surface. Reference number 723 is a flat, water- and heat-proof surface. Reference number 731 is a male mold. Reference number 732 is a female mold. Reference number 733 is a small hole, extending from the base of the female mold interior to the exterior surface of the female mold structure. Reference number 741 is a hollow tube, delivering ground (or chopped, shredded, powdered, foamed, crystalline, or whole) combustible material. Reference number 751 is a crimping machine. Reference number 752 is an enclosed, single-serve, prepackaged combustible material unit. Reference number 760 is a rotationally movable structure. Reference number 771 is a translationally movable structure. Reference number 772 is a pin, nominally smaller than the corresponding hole in the female mold (pictured here in its inverted orientation). Reference number 781 is a prepackaged combustible material unit, releasing from the female mold (to be optionally further processed into secondary, tertiary, quaternary, etc. packaging).

FIG. 8 illustrates a subset of the steps from the aforementioned method of making prepackaged combustible material, this time at mass scale. Reference number 811 is a number of de-stemmed leaves, optionally comprised of the same species as that contained within the prepackaged combustible material units. Reference number 812 is a sheet produced from said leaves. Reference number 821 is a tube delivering steam. Reference number 822 is a surface comprised of small holes, distributing the steam evenly across the entirety of the two dimensional surface. Reference number 823 is a conveyor belt. Reference number 831 is an array of male molds. Reference number 832 is an array of female molds. Reference number 833 is a rotationally movable support for the female mold assembly. Reference number 834 is that same rotationally movable support, mid rotation. Reference number 835 is that same rotationally movable support, flipped 180 degrees from its upright orientation. Reference number 841 is a branching structure, diverting and apportioning the combustible material (whether ground, chopped, shredded, powdered, foamed, crystalline, or whole) into single-servings defined by the aforementioned mold structure. Reference number 842 is a crimping machine. Reference number 851 is a pin array. Reference number 861 is an array of prepackaged combustible material units, releasing from the female mold due to the combination of gravity and a nudge imparted by the pin array. Reference number 862 is a container to receive the prepackaged combustible material units (which may then optionally undergo secondary (e.g., packages of 20), tertiary (e.g., cartons of a dozen packages), and quaternary (e.g., boxes of 10 cartons) packaging operations).

ADDITIONAL EMBODIMENTS

Embodiment A

According to an embodiment, a method of making a prepackaged, combustible unit of a material for use in an inhalation system comprising a metered dose inhaler or a dry powder inhaler, is disclosed. The method comprising: creating and shaping a combustible material packaging; placing a combustible material within the combustible material packaging; and sealing the combustible material packaging around the combustible material to create a prepackaged, combustible unit.

Embodiment B

The method of Embodiment A, wherein creating and shaping the combustible material packaging comprises: processing leaves or plant fibers into a fibrous sheet; steaming the fibrous sheet to create a steamed fibrous sheet of combustible material packaging; and pressing the steamed fibrous sheet of combustible material packaging into a molding apparatus comprising a female mold using a corresponding male mold to create a shaped combustible material packaging comprising an open space pocket disposed therein.

Embodiment C

The method of Embodiment B, wherein steaming the fibrous sheet comprises using a steam tube and diffusor plate.

Embodiment D

The method of Embodiment B, wherein placing the combustible material within the combustible material packaging comprises: filling the open space pocket disposed in the shaped combustible material packaging with granules of the combustible material.

Embodiment E

The method of Embodiment D, wherein filling the open space pocket comprises dispensing the granules of combustible material from a hollow tube or using a branching structure.

Embodiment F

The method of Embodiment E, wherein the branching structure is one of a branched manifold, a granular conveyance, or a feed manifold.

Embodiment G

The method of Embodiment D, wherein sealing the combustible material packaging around the combustible material comprises: after filling the open space pocket disposed in the shaped combustible material packaging with the combustible material, separating a flap portion of the combustible material packaging surrounding the opening of the open space pocket; and pinching or crimping the flap portion of the combustible material packaging surrounding the filled open space pocket using a machine to seal the combustible material packaging around the combustible material disposed therein, creating the prepackaged, combustible unit.

Embodiment H

The method of Embodiment G, wherein the prepackaged, combustible unit comprises a shape selected from the group consisting of pill-shape, oblong, capsule, octagonal prism, heptagonal prism, hexagonal prism, pentagonal prism, rectangular prism, triangular prism, cylinder, sphere, tetrahedron, rhombic dodecahedron, truncated octahedron, droplet, pouch, and pod.

Embodiment I

The method of Embodiment I, further comprising holding the created prepackaged, combustible unit inside the molding apparatus; and flipping the molding apparatus upside down into an inverted position.

Embodiment J

The method of Embodiment I, further comprising inserting a set of pins into a back end of the molding apparatus when in the inverted position, wherein each of the pins in the set of pins contacts a corresponding prepackaged combustible unit, pushing the corresponding prepackaged combustible unit onto a conveyor belt or into a holding container for further processing.

Embodiment K

An inhalation device comprising a cap module detachably connected to a base module, wherein the cap module is configured to regulate air flow into or out of the base module and to retain a prepackaged combustible material; and wherein the base module is configured to supply, at a demand of a user, a constant pressure gradient for drawing air into an internal space disposed in the base module via the cap module.

Embodiment L

The inhalation device of Embodiment K, wherein the cap module comprises a standard connection part configured to allow the cap module to detachably connect to any one of a plurality of base modules having different configurations.

Embodiment M

The inhalation device of Embodiment K, wherein the base module in configured to supply the constant pressure gradient for a consistent or predetermined period of time, and when combusted, smoke from the prepackaged combustible material is drawn into an internal volume of the base module for inhalation by the user.

Embodiment N

The inhalation device of Embodiment K, wherein the cap module comprises a number of apertures configured to permit air flow, wherein a first aperture of the number of apertures is configured to receive the prepackaged combustible material and to permit air flow from an environment into the base module's internal space, and wherein a second aperture of the number of apertures is an access point at which a user inhales.

Embodiment O

The inhalation device of Embodiment N, further comprising a recess disposed within the first aperture, wherein the recess is configured to retain a unit or quantity of prepackaged combustible material that is sized and shaped to fit therein.

Embodiment P

The inhalation device of Embodiment N, wherein the second aperture does not permit air flow into the base module's internal space.

Embodiment Q

The inhalation device of Embodiment K, wherein the base module comprises one of an hourglass, a squeeze, a pipette, a venturi, or a lever configuration.

Embodiment R

The inhalation device of Embodiment Q, wherein the base module comprises an hourglass configuration including a body having two symmetrical halves defining a top chamber and a bottom chamber that are in fluid communication with at least one of a number of apertures in the cap module.

Embodiment S

The inhalation device of Embodiment R, wherein the cap module is detachably connected to the base module by one or more quick release connectors from the group consisting of a pair of magnets, a turn lug fastener, a spring lug fastener with a recess, and a j-slot release disposed on the base module and configured to be joined to corresponding quick release connectors of the cap module.

Embodiment T

The inhalation device of Embodiment S, wherein the cap module is detachably connected to the base module by a pair of magnets on the base module configured to be joined to corresponding magnets of the cap module.

Embodiment U

The inhalation device of Embodiment S, further comprising a translationally movable valve configured to regulate flow between the top chamber and the bottom chamber.

Embodiment V

The inhalation device of Embodiment S, wherein the translationally movable valve comprises a directional valve that is translationally movable within, but also bounded by, a relative position of the directional valve, and wherein the directional valve comprises sealing characteristics that are determined by gravity.

Embodiment W

The inhalation device of Embodiment Q, wherein the base module comprises a squeeze configuration including an elastically compressible bulb that hydraulically modulates a position of a plug residing within a tube, wherein a top end of the tube is configured to connect to the cap module via a quick release connector.

Embodiment X

The inhalation device of Embodiment Q, wherein the top end of the tube is configured to magnetically connect to the cap module.

Embodiment Y

The inhalation device of Embodiment X, wherein in response to the bulb being squeezed, an incompressible fluid disposed with the tube presses the plug towards the top end, and in response to the bulb being released or unsqueezed, the plug is drawn back toward the bulb, creating low pressure in a top portion of the tube and drawing smoke from a bowl disposed in the cap module.

Embodiment Z

The inhalation device of claim Embodiment Q, wherein the base module comprises a pipette configuration comprising two tubes of different diameters and approximately a same length, wherein the two tubes are connected by a flexible tube permitting fluid flow between the two tubes, and wherein a first of the two tubes includes a plunger with o-rings disposed therein which is configured to be depressed to cause a corresponding movement of a plug with second o-rings disposed in the second of the two tubes.

Embodiment AA

The inhalation device of Embodiment Q, wherein the base module comprises a venturi configuration comprising an enclosed loop including an impeller or propeller disposed therein and coupled to a motor via a gear shaft configured to induce water flow.

Embodiment AB

The inhalation device of Embodiment AA, wherein an interior of the enclosed loop comprises a portion of gradual constriction of the enclosed loop serving as a venturi valve, and a bulb disposed opposite the venturi valve of the enclosed loop.

Embodiment AC

The inhalation device of claim Q, wherein the base module comprises a lever configuration including a body chamber that fits into a base portion having a hole, and wherein the lever is spring loaded.

Embodiment AD

The inhalation device of Embodiment K, wherein the base module is configured to use forces including magnetic, gravitational, centrifugal, hydraulic, or a combination thereof to engender a low pressure necessary for an ingress of combusting material.

Embodiment AE

An inhalation device comprising an hourglass configuration utilizing a submodule having integrated ingress and egress apertures, wherein the integrated ingress apertures are configured to draw air into an internal space of the submodule for activating combustion of a prepackaged, metered dose of an organic material, and wherein the integrated egress apertures are configured to provide an access point for an amount of smoke produced by the combustion of the prepackaged, metered dose of the organic material, wherein the access point is configured to enable a user to inhale the amount of smoke.

Embodiment AF

The inhalation device of Embodiment AE wherein the submodule further comprises a bowl, a ball bearing, and an egress tube with a constriction having a circular cross section, and wherein the inhalation device does not include a cap module

Embodiment AG

An inhalation system providing a mechanized, replicable process for producing a quantity of product from, at least one of loose or prepackaged combustible material, wherein the system activates using a force including magnetic, gravitational, centrifugal, hydraulic, or a combination thereof, and wherein upon activation, a period of time passes before the combustible material has fully combusted.

Embodiment AH

The inhalation system of Embodiment AG, wherein the prepackaged combustible material comprises a combustible package and a predetermined amount of a combustible material.

Embodiment AI

The inhalation system of Embodiment AG, wherein the prepackaged combustible material comprises a shape selected from the group consisting of pill-shape, oblong, capsule, octagonal prism, heptagonal prism, hexagonal prism, pentagonal prism, rectangular prism, triangular prism, cylinder, sphere, tetrahedron, rhombic dodecahedron, truncated octahedron, droplet, pouch, and pod.

Embodiment AJ

A kit comprising the inhalation device of Embodiment K and instructions for use thereof.

Embodiment AK

The kit of Embodiment AJ, wherein the instructions comprise directing a user to: optionally, assemble the inhalation device from its constituent parts; fill a specific section of the inhalation device with water; place a unit of prepackaged combustible material or loose material into a bowl disposed in a cap module of the inhalation device; attach the cap module on top of a base module of the inhalation device; activate the inhalation device; hold a flame to the unit of prepackaged combustible material or to the loose material in the bowl; and after observing combustion of the unit of prepackaged combustible material or the loose material, inhale smoke through an inhalation aperture located in the cap module.

Embodiment AL

The kit of Embodiment AJ, wherein the instructions directing the user to activate the inhalation device comprise activating the inhalation device by one of pressing a button, pulling a lever, or squeezing a bulb.

Embodiment AM

The kit of Embodiment AK, wherein the cap module is attached to the base module of the inhalation device using magnets disposed on the cap module that align with corresponding magnets on the base module to confirm orientation.

Embodiment AN

The kit of Embodiment AJ, further comprising at least one unit of prepackaged combustible material.

Embodiment AO

The kit of Embodiment AN, wherein the at least one unit of prepackaged combustible material comprises a combustible package and a predetermined amount of a combustible material.

Embodiment AP

The kit of Embodiment AN, wherein the at least one unit of prepackaged combustible material comprises a shape selected from the group consisting of pill-shape, oblong, capsule, octagonal prism, heptagonal prism, hexagonal prism, pentagonal prism, rectangular prism, triangular prism, cylinder, sphere, tetrahedron, rhombic dodecahedron, truncated octahedron, droplet, pouch, and pod.

Embodiment AQ

A method of using an inhalation device, the method comprising: filling an upper chamber portion of the inhalation device with water; placing a standard cap module atop the upper chamber portion by aligning a number of magnets attached to the standard cap module with corresponding magnets disposed on a top part of the upper chamber portion; filling a recess disposed in the cap module with loose or prepackaged combustible material; activating the inhalation device by depressing a button while igniting the combustible material in the recess using a lighter or a match; continue pressing the button while the water flows from the upper chamber portion to a lower chamber of the inhalation device; placing one's lips on or over an inhalation aperture located in an edge of the cap module; and inhaling smoke from the chamber, while still pushing the button.

Embodiment AR

The method of Embodiment AQ, further comprising removing the cap module; flipping the inhalation device entirely over; and repeating the process steps, as desired.

Embodiment AS

A method for dosing and forming at mass scale, prepackaged, combustible units of a product for use in an inhalation device, comprising: processing leaves or plant fibers into fibrous sheets; steaming the fibrous sheets using a tube delivering steam and a two dimensional surface comprised of small holes configured to distribute the steam evenly across the entirety of the two dimensional surface to create steamed fibrous sheets of combustible material packaging; and systematically pressing the steamed fibrous sheets of combustible material packaging into a molding structure to create and shape single-serving combustible material packaging; using a branching structure, diverting and apportioning the combustible material into the single-serving combustion material packaging on the mold structure; and using a crimping machine, sealing the combustible material packaging around the combustible material to create the prepackaged, combustible material units; and separating the prepackaged combustible material units from each other.

Embodiment AT

A metered dose inhaler comprising a cap module detachably connected to a base module, wherein the cap module is configured to regulate air flow into or out of the base module, retain a prepackaged combustible material, and provide an inhalation aperture for a user to inhale an amount of smoke resulting from combustion of a metered amount of the prepackaged combustible material; wherein the base module is configured to supply, at a demand of a user, a constant pressure gradient for drawing air into an internal space disposed in the base module via the cap module, and wherein the base module comprises a pressurized propellant (e.g. air or nitrogen) to expel the amount of smoke through the inhalation aperture for inhalation by the user.

Embodiment AU

A metered dose inhaler comprising a cap module detachably connected to a base module, air flow into or out of the base module, retain a prepackaged combustible material, and provide an inhalation aperture for a user to inhale an amount of smoke resulting from combustion of a metered amount of the prepackaged combustible material; and wherein the base module is configured to supply, at a demand of a user, a constant pressure gradient for drawing air into an internal space disposed in the base module via the cap module, and expel the amount of smoke through the inhalation aperture for inhalation by the user without utilizing a pressurized propellant.

Embodiment AV

A modular, fluid mechanical system for producing, for medicinal or recreational consumption, a single-serving, prepackaged combustible unit of a plant based material for use in an inhalation system, a metered dose inhaler, or a dry powder inhaler.

Embodiment AW

The system of Embodiment AV, wherein the prepackaged combustible unit of the plant based material comprises a combustible package encasing a particulate core, the particulate core comprising a predetermined amount of the plant based combustible material.

Embodiment AX

A method of making, for medicinal or recreational consumption, a single-serving, prepackaged combustible unit of a material for use in an inhalation system, a metered dose inhaler, or a dry powder inhaler, the method comprising: processing leaves or plant fibers into a fibrous sheet; steaming the fibrous sheet using a diffusor plate and a steam tube, to create a steamed fibrous sheet; pressing the steamed fibrous sheet in a molding apparatus comprising a female mold and a corresponding male mold to create a number of single-serving, prepackaged combustible material packages comprising open spaces with pockets disposed therein, each open space and corresponding pocket corresponding to a different, individual single-serving, prepackaged combustible material package; filling the each open space pocket using a branching manifold and dispensing a predetermined amount of granules of the combustible material in the each open space pocket; after filling the each open space pockets disposed in the shaped combustible material packaging with the combustible material, separating a flap portion of the combustible material packaging surrounding an opening of the each filled open space pocket; pinching or crimping the flap portion of the combustible material packaging surrounding the each filled open space pockets using a machine to seal the combustible material packaging around the combustible material disposed therein, creating the prepackaged, combustible unit; holding the created prepackaged, combustible unit inside the molding apparatus; and flipping the molding apparatus upside down into an inverted position; inserting a set of pins into a back end of the molding apparatus when in the inverted position, wherein each of the pins in the set of pins contacts a corresponding prepackaged combustible unit; and pushing the each corresponding prepackaged combustible unit onto a conveyor belt or into a holding container for further processing.

Embodiment AY

A method of using an inhalation system, the method comprising: pyrolyzing a fixed volume of plant matter across a constant pressure gradient for a fixed length of time; collecting smoke from the pyrolyzed plant matter into a bowl in fluid communication with at least one of a chamber or a venture valve; wherein the chamber comprises a volume (V) of the smoke that is increasing at a constant rate according to the formula $dV_{alamber}/dt = k1 > 0$ from $V_{min}$ at $t_0$ to $V_{max}$ at $t_0+t_f$, wherein $t_0$ is a beginning time at which V is at a minimum ($V_{min}$) and $t_f$ is a final time at which V is at a maximum ($V_{max}$); and wherein the venturi valve is disposed within a continuous loop tube containing an incompressible liquid exhibiting a nearly constant volumetric flux; and inhaling the smoke generated by the inhalation system into a user's lungs for medicinal or recreational use.

Embodiment AZ

A kit comprising the modular, fluid mechanical system of Embodiment AV and instructions for use thereof; and, optionally, one or more single serve pyrolyzable plant packets.

Embodiment AAA

A modular metered dose inhaler comprising a top releasably connected to a base, the base having a variable internal volume; the top having a combustion bowl configured to receive and combust combustible material to produce smoke, the combustion bowl in fluid communication with the variable internal volume of the base such that the smoke travels from the combustion bowl to the internal volume of the base; and the top having an inhalation aperture, the inhalation aperture in one-way fluid communication with the variable internal volume of the base such that smoke travels from the internal volume of the base to a user via the inhalation aperture; wherein the variable internal volume is varied in response to (i) a mechanically induced input by a user and/or (ii) fluid flowing through the internal volume of the base; and wherein in response to varying the internal volume, a metered quantity of smoke is stored within the internal volume of the base.

Embodiment AAB

The metered dose inhaler of Embodiment AAA, wherein the mechanically induced input by a user provides a constant pressure gradient between the combustion bowl and the internal volume of the base over a repeatable, defined unit of time.

Embodiment AAC

The metered dose inhaler of Embodiment AAB, further comprising a prepackaged combustible material configured to be received by the combustion bowl and further disposed therein.

Embodiment AAD

The metered dose inhaler of Embodiment AAC, wherein the prepackaged combustible material comprises cannabis.

Embodiment AAE

The metered dose inhaler of Embodiment AAB, wherein the base further comprises a venturi disposed therein, wherein fluid within the base flows through the venturi and provides the constant pressure gradient.

Embodiment AAF

The metered dose inhaler of Embodiment AAA, wherein the base comprises an hourglass configuration including a body having two symmetrical halves defining a top chamber and a bottom chamber controlled by a translationally movable valve configured to regulate flow between the top chamber and the bottom chamber.

Embodiment AAG

The metered dose inhaler of Embodiment AAA, wherein the base comprises a squeeze configuration including an elastically compressible bulb that hydraulically modulates a position of a plug residing within a tube having an upper end and a lower end; wherein in response to the bulb being squeezed, an incompressible fluid disposed within the tube presses the plug towards the upper end, and in response to the bulb being released or unsqueezed, the plug is drawn back toward the lower end of the bulb, creating low pressure in the upper end of the tube and drawing smoke from the combustion bowl.

Embodiment AAH

The metered dose inhaler of Embodiment AAA, wherein the base comprises a pipette configuration that allows fluid flow between different pipe portions of the base, and in response to pressure being applied in a first pipe, a plug moves the fluid through a second pipe.

Embodiment AAI

The metered dose inhaler of Embodiment AAA, wherein the base comprises a venturi configuration comprising an enclosed loop including an impeller or propeller disposed therein and coupled to a motor via a gear shaft configured to induce fluid flow, wherein an interior of the enclosed loop comprises a constriction serving as a venturi valve and a bulb disposed opposite the venturi valve of the enclosed loop.

Embodiment AAJ

The metered dose inhaler of Embodiment AAA, wherein the base comprises a lever configuration including a body chamber inside of a base portion having a hole, wherein the lever is spring loaded.

Embodiment AAK

A metered dose inhaler of Embodiment AAA, wherein the base is releasably connected to the top via a quick release connector.

Embodiment AAL

A method of using a metered dose inhaler comprising a top releasably connected to a base, the base having a variable internal volume, the method comprising filling a chamber portion of the base with water; connecting the top to the base using releasable connectors to confirm orientation; placing one unit of prepackaged combustible material into a combustion bowl disposed in the top, the combustion bowl configured to receive and combust the combustible material to produce smoke, and the combustion bowl in fluid communication with the variable internal volume of the base such that the smoke travels from the combustion bowl to the internal volume of the base; activating the device to enable fluid to flow from the combustion bowl and into the variable internal volume of the base; holding a flame to the prepackaged combustible material, causing combustion thereof; after observing the prepackaged material combust fully, inhaling the smoke through an inhalation aperture disposed in the top, the inhalation aperture in one-way fluid communication with the variable internal volume of the base such that smoke travels from the internal volume of the base to a user via the inhalation; and equalizing pressure in the chamber portion from which smoke is being inhaled by a continued activation of the device.

Embodiment AAM

The method of using a metered dose inhaler according to Embodiment AAL, wherein activating the device comprises creating a pressure differential across the base to enable the smoke to travel from the combustion bowl to the internal volume of the base.

Embodiment AAN

The method of using a metered dose inhaler according to Embodiment AAL, further comprising assembling the metered dose inhaler from its constitutent parts prior to filling the base with water.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A modular metered dose inhaler comprising a top releasably connected to a base,
    the base having a variable internal volume;
    the top having a combustion bowl configured to receive and combust combustible material to produce smoke, the combustion bowl in fluid communication with the variable internal volume of the base such that the smoke travels from the combustion bowl to the internal volume of the base; and
    the top having an inhalation aperture, the inhalation aperture in one-way fluid communication with the variable internal volume of the base such that smoke travels from the internal volume of the base to a user via the inhalation aperture;
    wherein the variable internal volume is varied in response to (i) a mechanically induced input by a user and/or (ii) fluid flowing through the internal volume of the base;
    wherein the mechanically induced input by a user provides a constant pressure gradient between the combustion bowl and the internal volume of the base over a repeatable, defined unit of time; and
    wherein in response to varying the internal volume, a metered quantity of smoke is stored within the internal volume of the base.

2. The metered dose inhaler of claim 1 further comprising a prepackaged combustible material configured to be received by the combustion bowl and further disposed therein.

3. The metered dose inhaler of claim 2 wherein the prepackaged combustible material comprises cannabis.

4. The metered dose inhaler of claim 1 wherein the base further comprises a venturi disposed therein, wherein fluid within the base flows through the venturi and provides the constant pressure gradient.

5. The metered dose inhaler of claim 1 wherein the base comprises an hourglass configuration including a body having two symmetrical halves defining a top chamber and a bottom chamber controlled by a translationally movable valve configured to regulate flow between the top chamber and the bottom chamber.

6. The metered dose inhaler of claim 1 wherein the base comprises a squeeze configuration including an elastically compressible bulb that hydraulically modulates a position of a plug residing within a tube having an upper end and a lower end;
    wherein in response to the bulb being squeezed, an incompressible fluid disposed within the tube presses the plug towards the upper end, and in response to the bulb being released or unsqueezed, the plug is drawn back toward the lower end of the bulb, creating low pressure in the upper end of the tube and drawing smoke from the combustion bowl.

7. The metered dose inhaler of claim 1 wherein the base comprises a pipette configuration that allows fluid flow between different pipe portions of the base, and in response to pressure being applied in a first pipe, a plug moves the fluid through a second pipe.

8. The metered dose inhaler of claim 1 wherein the base comprises a venturi configuration comprising an enclosed loop including an impeller or propeller disposed therein and coupled to a motor via a gear shaft configured to induce fluid flow, wherein an interior of the enclosed loop comprises a constriction serving as a venturi valve and a bulb disposed opposite the venturi valve of the enclosed loop.

9. The metered dose inhaler of claim 1 wherein the base comprises a lever configuration including a body chamber inside of a base portion having a hole, wherein the lever is spring loaded.

10. The metered dose inhaler of claim 1 wherein the base is releasably connected to the top via a quick release connector.

11. A modular metered dose inhaler comprising a top releasably connected to a base,
    the base having a variable internal volume;
    the top having a combustion bowl configured to receive and combust a prepackaged combustible material comprising a predetermined amount of cannabis to produce smoke, the combustion bowl in fluid communication with the variable internal volume of the base such that the smoke travels from the combustion bowl to the internal volume of the base; and
    the top having an inhalation aperture, the inhalation aperture in one-way fluid communication with the variable internal volume of the base such that smoke travels from the internal volume of the base to a user via the inhalation aperture;

wherein the variable internal volume is varied in response to (i) a mechanically induced input by a user and/or (ii) fluid flowing through the internal volume of the base; and wherein in response to varying the internal volume, a metered quantity of smoke is stored within the internal volume of the base, wherein the base comprises an hourglass configuration including a body having two symmetrical halves defining a top chamber and a bottom chamber controlled by a translationally movable valve configured to regulate flow between the top chamber and the bottom chamber.

12. A modular metered dose inhaler comprising a top releasably connected to a base, the base having a variable internal volume;

the top having a combustion bowl configured to receive and combust a prepackaged combustible material comprising a predetermined amount of cannabis to produce smoke, the combustion bowl in fluid communication with the variable internal volume of the base such that the smoke travels from the combustion bowl to the internal volume of the base; and the top having an inhalation aperture, the inhalation aperture in one-way fluid communication with the variable internal volume of the base such that smoke travels from the internal volume of the base to a user via the inhalation aperture;

wherein the variable internal volume is varied in response to (i) a mechanically induced input by a user and/or (ii) fluid flowing through the internal volume of the base; and wherein in response to varying the internal volume, a metered quantity of smoke is stored within the internal volume of the base, wherein the base comprises a squeeze configuration including an elastically compressible bulb that hydraulically modulates a position of a plug residing within a tube having an upper end and a lower end;

wherein in response to the bulb being squeezed, an incompressible fluid disposed within the tube presses the plug towards the upper end, and in response to the bulb being released or unsqueezed, the plug is drawn back toward the lower end of the bulb, creating low pressure in the upper end of the tube and drawing smoke from the combustion bowl.

13. A modular metered dose inhaler comprising a top releasably connected to a base, the base having a variable internal volume;

the top having a combustion bowl configured to receive and combust a prepackaged combustible material comprising a predetermined amount of cannabis to produce smoke, the combustion bowl in fluid communication with the variable internal volume of the base such that the smoke travels from the combustion bowl to the internal volume of the base; and the top having an inhalation aperture, the inhalation aperture in one-way fluid communication with the variable internal volume of the base such that smoke travels from the internal volume of the base to a user via the inhalation aperture;

wherein the variable internal volume is varied in response to (i) a mechanically induced input by a user and/or (ii) fluid flowing through the internal volume of the base; and wherein in response to varying the internal volume, a metered quantity of smoke is stored within the internal volume of the base, wherein the base comprises a pipette configuration that allows fluid flow between different pipe portions of the base, and in response to pressure being applied in a first pipe, a plug moves the fluid through a second pipe.

14. A modular metered dose inhaler comprising a top releasably connected to a base, the base having a variable internal volume;

the top having a combustion bowl configured to receive and combust a prepackaged combustible material comprising a predetermined amount of cannabis to produce smoke, the combustion bowl in fluid communication with the variable internal volume of the base such that the smoke travels from the combustion bowl to the internal volume of the base; and the top having an inhalation aperture, the inhalation aperture in one-way fluid communication with the variable internal volume of the base such that smoke travels from the internal volume of the base to a user via the inhalation aperture;

wherein the variable internal volume is varied in response to (i) a mechanically induced input by a user and/or (ii) fluid flowing through the internal volume of the base; and wherein in response to varying the internal volume, a metered quantity of smoke is stored within the internal volume of the base, wherein the base comprises a venturi configuration comprising an enclosed loop including an impeller or propeller disposed therein and coupled to a motor via a gear shaft configured to induce fluid flow, wherein an interior of the enclosed loop comprises a constriction serving as a venturi valve and a bulb disposed opposite the venturi valve of the enclosed loop.

15. The metered dose inhaler of claim 11 wherein the base is releasably connected to the top via a quick release connector.

16. The metered dose inhaler of claim 12 wherein the base is releasably connected to the top via a quick release connector.

17. The metered dose inhaler of claim 13 wherein the base is releasably connected to the top via a quick release connector.

18. The metered dose inhaler of claim 14 wherein the base is releasably connected to the top via a quick release connector.

19. The metered dose inhaler of claim 10 wherein the quick release connector comprises a pair of magnets, a ¼ turn lug, a spring lug with a recess, or a j-slot release.

20. The metered dose inhaler of claim 15 wherein the quick release connector comprises a pair of magnets, a ¼ turn lug, a spring lug with a recess, or a j-slot release.

21. The metered dose inhaler of claim 16 wherein the quick release connector comprises a pair of magnets, a ¼ turn lug, a spring lug with a recess, or a j-slot release.

22. The metered dose inhaler of claim 17 wherein the quick release connector comprises a pair of magnets, a ¼ turn lug, a spring lug with a recess, or a j-slot release.

23. The metered dose inhaler of claim 18 wherein the quick release connector comprises a pair of magnets, a ¼ turn lug, a spring lug with a recess, or a j-slot release.

\* \* \* \* \*